(12) United States Patent
Murakami et al.

(10) Patent No.: US 8,187,729 B2
(45) Date of Patent: May 29, 2012

(54) ORGANIC ELECTROLUMINESCENCE DEVICE

(75) Inventors: Takeshi Murakami, Kanagawa (JP); Ikuo Kinoshita, Kanagawa (JP); Kazunari Yagi, Kanagawa (JP); Saki Takada, Kanagawa (JP); Akira Takeda, Kanagawa (JP); Wataru Sotoyama, Kanagawa (JP); Hiroo Takizawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 911 days.

(21) Appl. No.: 12/210,594

(22) Filed: Sep. 15, 2008

(65) Prior Publication Data

US 2009/0072726 A1   Mar. 19, 2009

(30) Foreign Application Priority Data

Sep. 14, 2007   (JP) ................................. 2007-239652
Dec. 20, 2007   (JP) ................................. 2007-329145
Jul. 28, 2008   (JP) ................................. 2008-194095

(51) Int. Cl.
*H01L 51/54* (2006.01)
*C09K 11/06* (2006.01)

(52) U.S. Cl. ........ 428/690; 428/917; 313/504; 313/506; 252/301.16; 257/40; 257/102; 257/E51.044; 546/4

(58) Field of Classification Search ........................ None
See application file for complete search history.

(56) References Cited

U.S. PATENT DOCUMENTS 6,303,231 B1   10/2001   Sawada et al.
(Continued)

FOREIGN PATENT DOCUMENTS

EP   0969532 A2   1/2000
(Continued)

OTHER PUBLICATIONS

Chinese Office Action issued in corresponding Chinese Patent Application No. 200810215751.X on May 13, 2011.

(Continued)

*Primary Examiner* — Jennifer Chriss
*Assistant Examiner* — Michael H Wilson
(74) *Attorney, Agent, or Firm* — Sughrue Mion, PLLC

(57) ABSTRACT

A process for preparing a platinum complex represented by the following formula (1) includes reacting a compound represented by the following formula (B-2) and a compound represented by the following formula (B-2') with a compound represented by the following formula (A-0) to obtain a compound represented by the following formula (C-0); and reacting the compound represented by the formula (C-0) with a platinum salt:

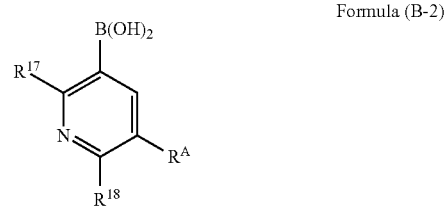

Formula (B-2)

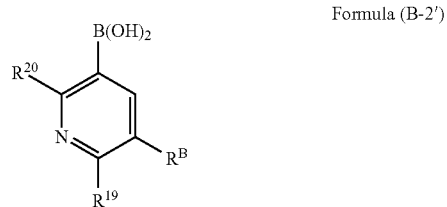

Formula (B-2')

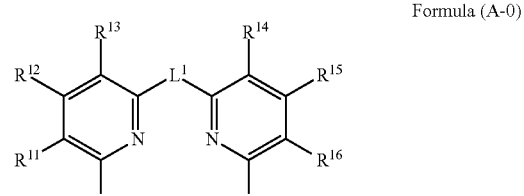

Formula (A-0)

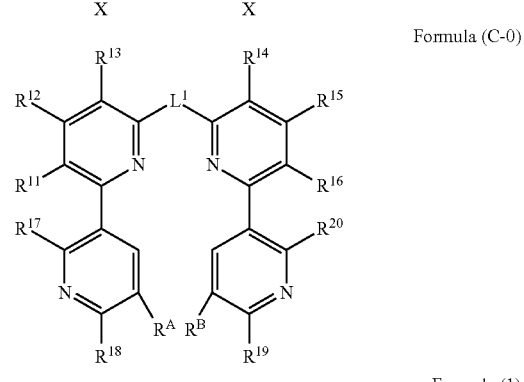

Formula (C-0)

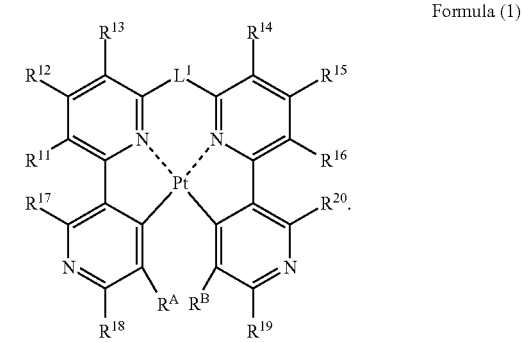

Formula (1)

6 Claims, No Drawings

U.S. PATENT DOCUMENTS

| | | |
|---|---|---|
| 6,303,238 B1 | 10/2001 | Thompson et al. |
| 6,653,654 B1 | 11/2003 | Che |
| 7,569,692 B2 | 8/2009 | Nii et al. |
| 2002/0008233 A1 | 1/2002 | Forrest et al. |
| 2002/0013306 A1 | 1/2002 | Lowe |
| 2002/0068190 A1 | 6/2002 | Tsuboyama et al. |
| 2003/0205707 A1 | 11/2003 | Chi-Ming |
| 2005/0170209 A1 | 8/2005 | Lee et al. |
| 2006/0073359 A1 | 4/2006 | Ise et al. |
| 2006/0134460 A1 | 6/2006 | Kondakova et al. |
| 2006/0134461 A1 | 6/2006 | Huo et al. |
| 2006/0182992 A1 | 8/2006 | Nii et al. |
| 2006/0204787 A1 | 9/2006 | Sano et al. |
| 2006/0263635 A1 | 11/2006 | Ise et al. |
| 2006/0264625 A1 | 11/2006 | Nakayama et al. |
| 2006/0286406 A1 | 12/2006 | Igarashi et al. |
| 2007/0082284 A1 | 4/2007 | Stoessel |
| 2007/0103060 A1 | 5/2007 | Itoh et al. |
| 2008/0001530 A1 | 1/2008 | Ise et al. |
| 2008/0036373 A1 | 2/2008 | Itoh et al. |
| 2009/0128008 A1 | 5/2009 | Ise |
| 2009/0174324 A1 | 7/2009 | Nii et al. |
| 2009/0261721 A1 | 10/2009 | Murakami |
| 2009/0267500 A1 | 10/2009 | Kinoshita et al. |

FOREIGN PATENT DOCUMENTS

| | | |
|---|---|---|
| EP | 1683804 A2 | 7/2006 |
| JP | 05-009470 A | 1/1993 |
| JP | 2000-048960 A | 2/2000 |
| JP | 2000-503982 T | 4/2000 |
| JP | 2001-338768 A | 7/2001 |
| JP | 2002-175884 A | 6/2002 |
| JP | 2002-305083 A | 10/2002 |
| JP | 2002-363552 A | 12/2002 |
| JP | 2003-123976 A | 4/2003 |
| JP | 2003-123981 A | 4/2003 |
| JP | 2003-520391 T | 7/2003 |
| JP | 2004-331508 A | 11/2004 |
| JP | 2005-220136 A | 8/2005 |
| JP | 2005-310733 A | 11/2005 |
| JP | 2006-093542 A | 4/2006 |
| JP | 2006-120811 A | 5/2006 |
| JP | 2006-182921 A | 7/2006 |
| JP | 2006-256999 A | 9/2006 |
| JP | 2006-261623 A | 9/2006 |
| JP | 2006-332620 A | 12/2006 |
| JP | 2007-19462 A | 1/2007 |
| JP | 2007-073845 | 3/2007 |
| JP | 2007-161673 A | 6/2007 |
| JP | 2007-519614 T | 7/2007 |
| JP | 2007-217364 A | 8/2007 |
| JP | 2008-037848 A | 2/2008 |
| JP | 2008-103535 | 5/2008 |
| JP | 2008-524848 T | 7/2008 |
| WO | 00-057676 A1 | 9/2000 |
| WO | 03-093283 A1 | 11/2003 |
| WO | 2004-039914 A1 | 5/2004 |
| WO | 2004/108857 A1 | 12/2004 |
| WO | 2005-042444 A2 | 5/2005 |
| WO | 2005/042550 A1 | 5/2005 |
| WO | 2008/117889 A1 | 10/2008 |

OTHER PUBLICATIONS

Extended European Search Report dated Dec. 11, 2008.

Yong-Yue Lin, et al.; "Structural, Photophysical, and Electrophosphorescent Properties of Platinum(II) Complexes Supported by Tetradentate N2O2 Chelates" Chemistry: A European Journal vol. 9, No. 6; 2003 Wiley-VCH; pp. 1263-1272.

M. A. Baldo, et al.; "Highly efficient phosphorescent emission from organic electroluminescent devices"; Letters to Nature, vol. 395; Sep. 1998; pp. 151-154.

Japanese Office Action issued in Application No. 2008-194095, dated Nov. 17, 2009.

Specification and Claims, New Application Transmittal and Amendment to the Specification, as filed in the U.S. Appl. No. 12/395,542.

Japanese Office Action issued in Application No. 2008-194095, dated Jan. 20, 2010.

ORGANIC ELECTROLUMINESCENCE DEVICE

BACKGROUND OF THE INVENTION

1. Field of the Invention

The present invention relates to a platinum complex compound useful as a light emitting material and an organic electroluminescence device (which may hereinafter be called "organic EL device") using the platinum complex compound.

2. Description of the Related Art

Research and development on organic electroluminescence devices are actively performed in recent years because they provide high-luminance emission at a low driving voltage. In general, organic EL devices have organic layers including a light emitting layer and a pair of electrodes sandwiching the organic layers therebetween. Electrons injected from a cathode and holes injected from an anode recombine in the light emitting layer and energy of excitons thus formed is made use of for light emission.

Use of a phosphorescent material has accelerated improvement in efficiency of devices. As the phosphorescent material, iridium complexes and platinum complexes are known (JP-A-2005-220136).

There is a report on the use of platinum complexes having a tetradentate for obtaining organic EL devices having improved emission efficiency and durability (International Patent Publication No. 04-108857). Of these platinum complexes, complexes having a pyridylpyridine skeleton enable shortening of an emission wavelength compared with complexes having a phenylpyridine skeleton so that they are promising as materials emitting light of from light-blue to blue color. It is however difficult to control generation of complexation byproducts so that establishment of a practical preparation process of them is required.

There is also a report on a blue light emitting material having a pyridylpyrazole skeleton and an organic EL device using it (JP-A-2007-19462), but this development has not succeeded in obtaining a device satisfying both high efficiency and durability particularly when it is used as a high luminance device. In consideration of the applications of organic EL devices to lighting apparatuses, however, use of them as a high luminance device is required. There is accordingly a demand for the development of blue-light emitting materials showing excellent durability even if they are used for such a high luminance device.

SUMMARY OF THE INVENTION

An object of the invention is to provide a preparation process of a pyridylpyridine platinum complex having a specific structure permitting improvement of a yield in a complexation step; a platinum complex prepared by the preparation process; a pyridylpyridine platinum complex having a specific structure; and an organic electroluminescence device having excellent durability when used as a high luminance device.

The present inventors have investigated with a view to overcoming the above-described problem and considered that a poor yield of the complexation step of a pyridylpyridine ligand and a platinum (II) salt owes to the coordination of the nitrogen atom of the pyridine ring to platinum. As a result, it has been found that a pyridylpyridine complex can be synthesized in a high yield by introducing an electron withdrawing substituent to the α-position relative to the nitrogen atom of the pyridine ring to control the coordination of the nitrogen atom to platinum (effective for reducing coordination of the nitrogen atom to platinum by the steric repulsion and reducing electron density on the nitrogen atom). It has also been found that the resulting pyridylpyridine complex shows improved durability in use for an organic EL device at high luminance compared with known blue-light emitting materials, leading to the completion of the invention. The present invention is therefore achieved by the following means.

(1) A process for preparing a platinum complex represented by the following formula (1), the process comprising:
reacting a compound represented by the following formula (B-2) and a compound represented by the following formula (B-2') with a compound represented by the following formula (A-0) to obtain a compound represented by the following formula (C-0); and
reacting the compound represented by the formula (C-0) with a platinum salt:

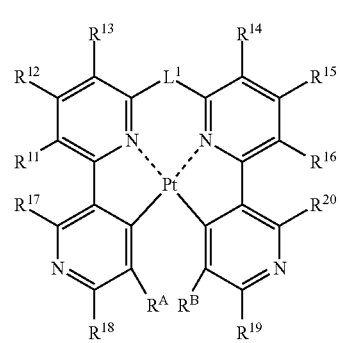

Formula (1)

wherein
each of $R^{11}$, $R^{12}$, $R^{13}$, $R^{14}$, $R^{15}$, $R^{16}$, $R^A$ and $R^B$ independently represents a hydrogen atom or a substituent,
each of $R^{17}$, $R^{18}$, $R^{19}$, and $R^{20}$ independently represents a hydrogen atom or a substituent, with the proviso that at least one of $R^{17}$ and $R^{18}$ represents an electron withdrawing substituent and at least one of $R^{19}$ and $R^{20}$ represents an electron withdrawing substituent, and
$L^1$ represents a single bond or a divalent linking group,

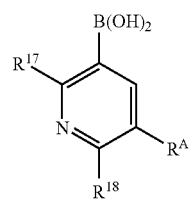

Formula (B-2)

wherein
each of $R^{17}$ and $R^{18}$ independently represents a hydrogen atom or a substituent, with the proviso that at least one of $R^{17}$ and $R^{18}$ represents an electron withdrawing substituent, and
$R^A$ represents a hydrogen atom or a substituent,

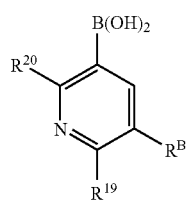

Formula (B-2')

wherein
each $R^{19}$ and $R^{20}$ independently represents a hydrogen atom or a substituent, with the proviso that at least one of $R^{19}$ and $R^{20}$ represents an electron withdrawing substituent, and $R^B$ represents a hydrogen atom or a substituent,

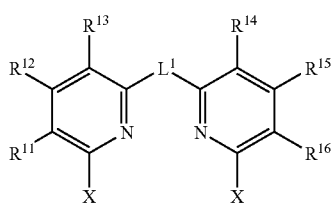

Formula (A-0)

wherein
each of $R^{11}$, $R^{12}$, $R^{13}$, $R^{14}$, $R^{15}$, and $R^{16}$ independently represents a hydrogen atom or a substituent,
$L^1$ represents a single bond or a divalent linking group, and
X represents a halogen atom,

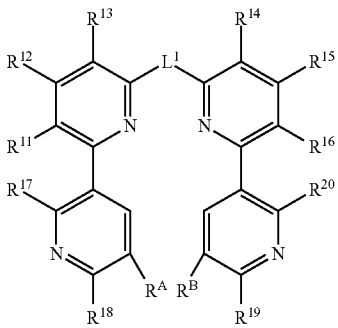

Formula (C-0)

wherein
each of $R^{11}$, $R^{12}$, $R^{13}$, $R^{14}$, $R^{15}$, $R^{16}$, $R^A$ and $R^B$ independently represents a hydrogen atom or a substituent,
each of $R^{17}$, $R^{18}$, $R^{19}$ and $R^{20}$ independently represents a hydrogen atom or a substituent, with the proviso that at least one of $R^{17}$ and $R^{18}$ represents an electron withdrawing substituent and at least one of $R^{19}$ and $R^{20}$ represents an electron withdrawing substituent, and
$L^1$ represents a single bond or a divalent linking group.
(2) A platinum complex represented by the following formula (1):

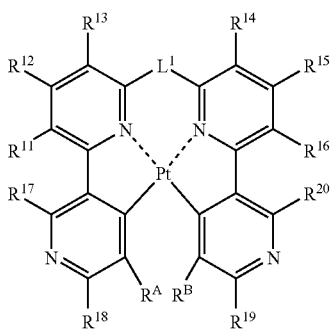

Formula (1)

wherein
each of $R^{11}$, $R^{12}$, $R^{13}$, $R^{14}$, $R^{15}$, $R^{16}$, $R^A$ and $R^B$ independently represents a hydrogen atom or a substituent,
each of $R^{17}$, $R^{18}$, $R^{19}$, and $R^{20}$ independently represents a hydrogen atom or a substituent, with the proviso that at least one of $R^{17}$ and $R^{18}$ represents an electron withdrawing substituent and at least one of $R^{19}$ and $R^{20}$ represents an electron withdrawing substituent, and
$L^1$ represents a single bond or a divalent linking group.

(3) A platinum complex as described in (2), wherein the formula (1) is represented by the following formula (2):

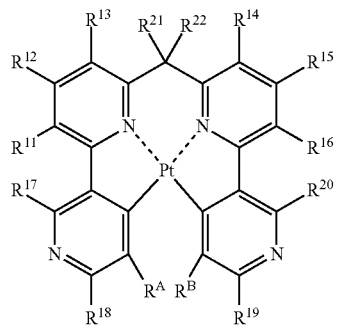

Formula (2)

wherein
$R^{11}$, $R^{12}$, $R^{13}$, $R^{14}$, $R^{15}$, $R^{16}$, $R^{17}$, $R^{18}$, $R^{19}$, $R^{20}$, $R^A$ and $R^B$ have the same meanings as defined in the formula (1), and
each of $R^{21}$ and $R^{22}$ independently represents a hydrogen atom or a substituent.
(4) A platinum complex obtained by the process as described in (1).
(5) An organic electroluminescence device comprising:
a pair of electrodes; and
at least one organic layer between the pair of electrodes, which contains at least one kind of the platinum complexes as described in (2), (3) and (4).
(6) An organic electroluminescence device comprising:
a pair of electrodes; and
at least one organic layer between the pair of electrodes, which comprises a light emitting layer containing at least one kind of the platinum complexes as described in (2), (3) and (4).

DETAILED DESCRIPTION OF THE INVENTION

According to the invention, respective platinum complexes represented by the formulas (1) and (2) can be prepared in a high yield. In addition, an organic electroluminescence device showing excellent durability when used as a high luminance device can be provided by incorporating these platinum complexes in the organic layers.

In this specification, Substituent Group B will be defined as follows.
(Substituent Group B)
Substituent group B includes alkyl groups (preferably $C_{1-30}$, more preferably $C_{1-20}$, especially preferably $C_{1-10}$ alkyl groups, such as methyl, ethyl, isopropyl, tert-butyl, n-octyl, n-decyl, n-hexadecyl, cyclopropyl, cyclopentyl, and cyclohexyl), alkenyl groups (preferably $C_{2-30}$, more preferably $C_{2-20}$, especially preferably $C_{2-10}$ alkenyl groups, such as vinyl, allyl, 2-butenyl, and 3-pentenyl), alkynyl groups (preferably $C_{2-30}$, more preferably $C_{2-20}$, especially preferably $C_{2-10}$ alkynyl groups such as propargyl and 3-pentynyl), aryl groups (preferably $C_{6-30}$, more preferably $C_{6-20}$, especially preferably $C_{6-12}$ aryl groups such as phenyl, p-methylphenyl, naphthyl, and anthranyl), amino groups (preferably $C_{0-30}$, more preferably $C_{0-20}$, especially preferably $C_{0-10}$ amino groups such as amino, methylamino, dimethylamino, diethylamino, dibenzylamino, diphenylamino, and ditolylamino), alkoxy groups (preferably $C_{1-30}$, more preferably $C_{1-20}$, especially preferably $C_{1-10}$ alkoxy groups such as methoxy, ethoxy, butoxy, and 2-ethylhexyloxy), aryloxy groups (preferably $C_{6-30}$, more preferably $C_{6-20}$, especially preferably $C_{6-12}$ aryloxy groups such as phenyloxy, 1-naphthyloxy, and 2-naphthyloxy), heterocyclic oxy groups (preferably $C_{1-30}$, more preferably $C_{1-20}$, especially preferably $C_{1-12}$ heterocyclic oxy groups such as pyridyloxy, pyrazyloxy, pyrimidyloxy, and quinolyloxy), acyl groups (preferably $C_{1-30}$, more preferably $C_{1-20}$, especially preferably $C_{1-12}$ acyl groups, such as acetyl, benzoyl, formyl, and pivaloyl), alkoxycarbonyl groups (preferably $C_{2-30}$, more preferably $C_{2-20}$, especially preferably $C_{2-12}$ alkoxycarbonyl groups such as methoxycarbonyl and ethoxycarbonyl), aryloxycarbonyl groups (preferably $C_{7-30}$, more preferably $C_{7-20}$, especially preferably $C_{7-12}$ aryloxycarbonyl groups such as phenyloxycarbonyl), acyloxy groups (preferably $C_{2-30}$, more preferably $C_{2-20}$, especially preferably $C_{2-10}$ acyloxy groups such as acetoxy and benzoyloxy), acylamino groups (preferably $C_{2-30}$, more preferably $C_{2-20}$, especially preferably $C_{2-10}$ acylamino groups such as acetylamino and benzoylamino), alkoxycarbonylamino groups (preferably $C_{2-30}$, more preferably $C_{2-20}$, especially preferably $C_{2-12}$ alkoxycarbonylamino groups such as methoxycarbonylamino), aryloxycarbonylamino groups (preferably $C_{7-30}$, more preferably $C_{7-20}$, especially preferably $C_{7-12}$ aryloxycarbonylamino groups such as phenyloxycarbonylamino), sulfonylamino groups (preferably $C_{1-30}$, more preferably $C_{1-20}$, especially preferably $C_{1-12}$ sulfonylamino groups such as methanesulfonylamino and benzenesulfonylamino), sulfamoyl groups (preferably $C_{0-30}$, more preferably $C_{0-20}$, especially preferably $C_{0-12}$ sulfamoyl groups such as sulfamoyl, methylsulfamoyl, dimethylsulfamoyl, and phenylsulfamoyl), carbamoyl groups (preferably $C_{1-30}$, more preferably $C_{1-20}$, especially preferably $C_{1-12}$ carbamoyl groups such as carbamoyl, methylcarbamoyl, diethylcarbamoyl, and phenylcarbamoyl), alkylthio groups (preferably $C_{1-30}$, more preferably $C_{1-20}$, especially preferably $C_{1-12}$ alkyltho groups such as methylthio and ethylthio), arylthio groups (preferably $C_{6-30}$, more preferably $C_{6-20}$, especially preferably $C_{6-12}$ arylthio groups such as phenylthio), heterocyclic thio groups (preferably $C_{1-30}$, more preferably $C_{1-20}$, especially preferably $C_{1-12}$ heterocyclic thio groups such as pyridylthio, 2-benzimidazolylthio, 2-benzoxazolylthio, and 2-benzthiazolylthio), sulfonyl groups (preferably $C_{1-30}$, more preferably $C_{1-20}$, especially preferably $C_{1-12}$ sulfonyl groups such as mesyl and tosyl), sulfinyl groups (preferably $C_{1-30}$, more preferably $C_{1-20}$, especially preferably $C_{1-12}$ sulfinyl groups such as methanesulfinyl and benzenesulfinyl), ureido groups (preferably $C_{1-30}$, more preferably $C_{1-20}$, especially preferably $C_{1-12}$ ureido groups such as ureido, methylureido, and phenylureido), phosphoric acid amide groups (preferably $C_{1-30}$, more preferably $C_{1-20}$, especially preferably $C_{1-12}$ phosphoric acid amide groups such as diethylphosphoric acid amide and phenylphosphoric acid amide), a hydroxy group, a mercapto group, halogen atoms (such as fluorine, chlorine, bromine, and iodine), a cyano group, a sulfo group, a carboxyl group, a nitro group, a hydroxamic acid group, a sulfino group, a hydrazino group, an imino group, heterocyclic (heteroaryl) groups (preferably $C_{1-30}$, more preferably $C_{1-12}$ heterocyclic groups having, for example, a nitrogen atom, an oxygen atom, or a sulfur atom as a heteroatom and specific examples include imidazolyl, pyridyl, quinolyl, furyl, thienyl, piperidyl, morpholino, benzoxazolyl, benzimidazolyl, benzthiazolyl, carbazolyl, and azepinyl), silyl groups (preferably $C_{3-40}$, more preferably $C_{3-30}$, especially preferably $C_{3-24}$ silyl groups such as trimethylsilyl and triphenylsilyl), and silyloxy groups (preferably $C_{3-40}$, more preferably $C_{3-30}$, especially preferably $C_{3-24}$ silyl groups such as trimethylsilyloxy and triphenylsilyloxy). These substituents may be substituted further.

The platinum complex represented by the formula (1) and having a tetradentate will next be described.

The hydrogen atoms in the description of the formulas (1) and (2) include an isotope (deuterium atom) and atoms constituting the substituent also include the isotope.

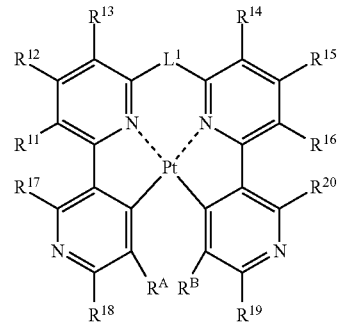

Formula (1)

In the formula (1), each of $R^{11}$, $R^{12}$, $R^{13}$, $R^{14}$, $R^{15}$, and $R^{16}$ independently represents a hydrogen atom or a substituent. The substituent represented by each of $R^{11}$, $R^{12}$, $R^{13}$, $R^{14}$, $R^{15}$, and $R^{16}$ has the same meaning as in Substituent group B. $R^{11}$, $R^{12}$, $R^{13}$, $R^{14}$, $R^{15}$, and $R^{16}$ may be, if possible, coupled together to form a ring.

Each of $R^{11}$ and $R^{16}$ represents preferably a hydrogen atom, an alkyl group, an aryl group, an amino group, an alkoxy group, an aryloxy group, an acyl group, an alkoxycarbonyl group, an alkylthio group, a sulfonyl group, a hydroxy group, a halogen atom, a cyano group, a nitro group, or a heterocyclic group, more preferably a hydrogen atom, an alkyl group, an aryl group, a halogen atom, a cyano group, or a heterocyclic group, still more preferably a hydrogen atom, a methyl group, a t-butyl group, a trifluoromethyl group, a phenyl group, a fluorine atom, a cyano group, or a pyridyl group, still more preferably a hydrogen atom, a methyl group, or a fluorine atom, especially preferably a hydrogen atom.

Each of $R^{13}$ and $R^{14}$ has preferably the same meaning as in the preferable range of $R^{11}$ and $R^{16}$.

Each of $R^{12}$ and $R^{15}$ represents preferably a hydrogen atom, an alkyl group, an aryl group, an amino group, an alkoxy group, an aryloxy group, an alkylthio group, an arylthio group, a halogen atom, a cyano group, or a heterocyclic group, more preferably a hydrogen atom, an alkyl group, an aryl group, an amino group, an alkoxy group, an aryloxy group, a halogen atom, or a heterocyclic group, still more preferably a hydrogen atom, an alkyl group, an amino group, an alkoxy group, a halogen atom, or a heterocyclic group, still more preferably a hydrogen atom, a methyl group, a t-butyl group, a dialkylamino group, a diphenylamino group, a methoxy group, a phenoxy group, a fluorine atom, an imidazolyl group, a pyrrolyl group, or a carbazolyl group, especially preferably a hydrogen atom, a methyl group a fluorine atom, a methoxy group, or a phenoxy group, and most preferably a hydrogen atom or a methyl group.

Each of $R^{17}$, $R^{18}$, $R^{19}$ and $R^{20}$ independently represents a hydrogen atom or a substituent. The substituent represented by each of $R^{17}$, $R^{18}$, $R^{19}$ and $R^{20}$ has the same meaning as in Substituent group B, with the proviso that at least one of $R^{17}$ and $R^{18}$ represents an electron withdrawing substituent and at least one of $R^{19}$ and $R^{20}$ represents an electron withdrawing substituent.

Preferred modes include a mode in which each of $R^{17}$ and $R^{20}$ represents an electron withdrawing substituent, a mode in which each of $R^{18}$ and $R^{19}$ represents an electron withdrawing substituent, a mode in which each of $R^{17}$, $R^{18}$, $R^{19}$ and $R^{20}$ represents an electron withdrawing substituent. More preferred modes include the mode in which each of $R^{17}$, $R^{18}$, $R^{19}$ and $R^{20}$ represents an electron withdrawing substituent. These plural substituents may be the same or different.

The term "electron withdrawing substituent" as used herein means a substituent having a Hammett σm constant or a Hammett σp constant greater than 0. In this specification, a substituent having at least one of a Hammett σm constant greater than 0 and a Hammett σp constant greater than 0 is defined as an electron with drawing group. The definition and values of the Hammett σ constant are reported in literature (for example, *Chem. Rev.*, 91, 165-195 (1991)).

Examples of each of $R^{17}$, $R^{18}$, $R^{19}$ and $R^{20}$ include a hydrogen atom, halogen atoms, fluorine-substituted phenyl groups, fluorine-substituted alkoxy groups, perfluoroalkyl groups, a cyano group, a nitro group, aryloxy groups, alkyl groups, aryl groups, silyl groups, trialkylsilyl groups, and tiarylsilyl groups.

Each of $R^{17}$, $R^{18}$, $R^{19}$ and $R^{20}$ represents preferably a hydrogen atom, a halogen atom, a fluorine-substituted phenyl group, a fluorine-substituted alkoxy group, a perfluoroalkyl group, a cyano group, a nitro group, or an aryloxy group, more preferably a hydrogen atom, a fluorine atom, a fluorine-substituted phenyl group, a trifluoromethoxy group, a trifluoromethyl group, a cyano group, or a phenoxy group, still more preferably a hydrogen atom, a fluorine atom, a perfluorophenyl group, a trifluoromethyl group, a cyano group, or a phenoxy group substituted with an electron withdrawing substituent, especially preferably a hydrogen atom, a fluorine atom, or a phenoxy group substituted with an electron withdrawing group, and most preferably a hydrogen atom or a fluorine atom.

The phenoxy group substituted with an electron withdrawing substituent is preferably a phenoxy group substituted with, as the electron withdrawing substituent, a fluorine atom, a trifluoromethyl group, or a cyano group, more preferably a phenoxy group substituted with a fluorine atom or a trifluoromethyl group. The number of the electron withdrawing substituents is preferably from 1 to 5, more preferably from 1 to 3, most preferably 1 or 2.

Each of $R^A$ and $R^B$ represents a hydrogen atom or a substituent. $R^A$ and $R^B$ may be linked to each other.

Each of $R^A$ and $R^B$ represents preferably a hydrogen atom, an alkyl group, an aryl group, an amino group, an alkoxy group, an aryloxy group, an acyl group, an alkoxycarbonyl group, an alkylthio group, a sulfonyl group, a hydroxy group, a halogen atom, a cyano group, a nitro group, or a heterocyclic group, more preferably a hydrogen atom, an alkyl group, an aryl group, an alkoxy group, an aryloxy group, an alkylthio group, a halogen atom, or a cyano group, still more preferably a hydrogen atom, an alkyl group, a perfluoroalkyl group, an aryl group, a halogen atom, or a cyano group, still more preferably a hydrogen atom, a methyl group, a trifluoromethyl group, or a cyano group, especially preferably a hydrogen atom, a trifluoromethyl group, a fluorine atom, or a cyano group, and most preferably a hydrogen atom.

$L^1$ represents a single bond or a divalent linking group. The divalent linking group is not particularly limited, but a linking group composed of a carbon atom, a nitrogen atom, an oxygen atom, a sulfur atom, or a silicon atom is preferred. The following are specific examples of the divalent linking group, but the invention is not limited to or by them.

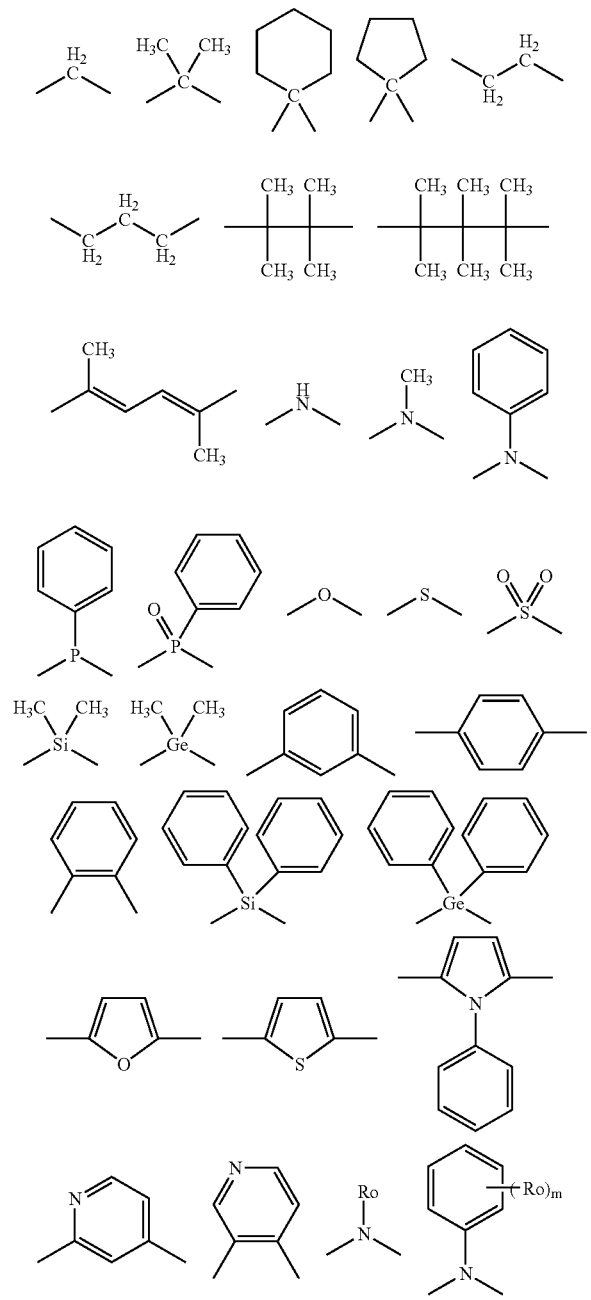

In the above formulas, Ro represents a substituent selected from Substituent Group B, preferably an alkyl group, more preferably a $C_{1-6}$ alkyl group; m stands for an integer from 0 to 5, preferably from 0 to 4, more preferably from 0 to 3.

$L^1$ represents preferably a dialkylmethylene group, a diarylmethylene group, or a diheteroarylmethylene group, more preferably a dimethylmethylene group, a methylphenylmethylene group or a diphenylmethylene group, still more preferably a dimethylmethylene group.

These linking groups may be substituted with a hydrogen atom. Examples of the substituent in this case correspond to those of Substituent Group B. When the linking group has two or more substituents, the substituents may be coupled together to form a ring.

The formulas (B-2) and (B-2') will next be described.

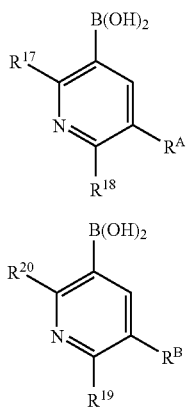

Formula (B-2)

Formula (B-2')

$R^{17}$, $R^{18}$, $R^{19}$, $R^{20}$, $R^A$ and $R^B$ in the formulas (B-2) and (B-2'), have the same meanings as defined in the formula (1) and preferable ranges of them are also the same as those in the formula (1).

The formula (A-0) will next be described.

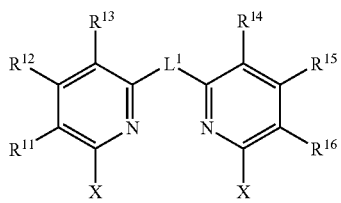

Formula (A-0)

$R^{11}$, $R^{12}$, $R^{13}$, $R^{14}$, $R^{15}$, $R^{16}$ and $L^1$ in the formula (A-0) have the same meanings as defined in the formula (1) and preferable ranges of them are also the same as those in the formula (1). X represents a hydrogen atom. The halogen atom is preferably a fluorine atom, a chlorine atom, a bromine atom, or an iodine atom more preferably a chlorine atom, a bromine atom, or an iodine atom, still more preferably a chlorine atom or a bromine atom.

The formula (C-0) will next be described.

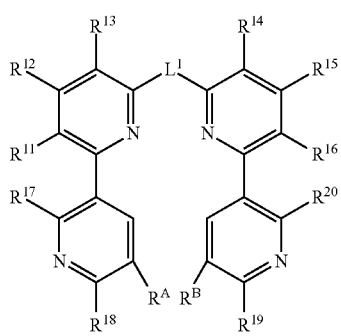

Formula (C-0)

$R^{11}$, $R^{12}$, $R^{13}$, $R^{14}$, $R^{15}$, $R^{16}$, $R^{17}$, $R^{18}$, $R^{19}$, $R^{20}$, $R^A$, $R^B$, and $L^1$ in the formula (C-0) have the same meanings as defined in the formula (1) and preferable ranges of them are also the same as those in the formula (1).

The platinum complex represented by the formula (1) is preferably a complex represented by the formula (2).

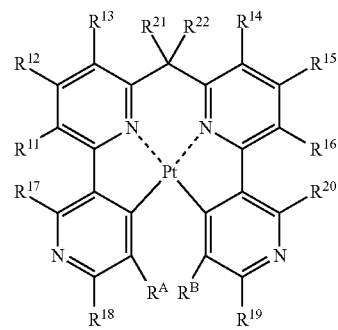

Formula (2)

$R^{11}$, $R^{12}$, $R^{13}$, $R^{14}$, $R^{15}$, $R^{16}$, $R^{17}$, $R^{18}$, $R^{19}$, $R^{20}$, $R^A$, and $R^B$ in the formula (2), have the same meanings as defined in the formula (1) and preferable ranges of them are also the same as those in the formula (1). Each of $R^{21}$ and $R^{22}$ independently represents a hydrogen atom or a substituent. The substituent represented by each of $R^{21}$ and $R^{22}$ has the same meaning as in Substituent Group B. Alternatively, $R^{21}$ and $R^{22}$ may combine with each other to form a cyclic structure, such as a cyclohexane ring or a cyclopentane ring.

Each of $R^{21}$ and $R^{22}$ is preferably a hydrogen atom, an alkyl group, an aryl group, a halogen atom or a heterocyclic group, more preferably a hydrogen atom, a methyl group, a phenyl group, a fluorine atom or a pyridyl group, still more preferably a methyl group, a phenyl group or a fluorine atom, most preferably a methyl group or a phenyl group.

The platinum complex represented by the formula (1) or (2) may be a low molecular compound, an oligomer compound, a high-molecular-weight compound (having a mass average molecular weight of preferably from 1000 to 5000000, more preferably from 5000 to 2000000, still more preferably from 10000 to 1000000) having the residue linked to the polymer chain, or a high-molecular-weight compound (having a mass average molecular weight of preferably from 1000 to 5000000, more preferably from 5000 to 2000000, still more preferably from 10000 to 1000000) having, in the main chain thereof, the structure of the platinum complex of the invention. When it is a high-molecular-weight compound, it may be a homopolymer or a copolymer with another polymer. The copolymer may be a random copolymer or a block copolymer. The copolymer may have, in the polymer thereof, a compound having a light emitting function and/or a compound having a charge transporting function.

The following are specific examples of the complex of the invention represented by the formula (1), but the invention is not limited to or by them.

1

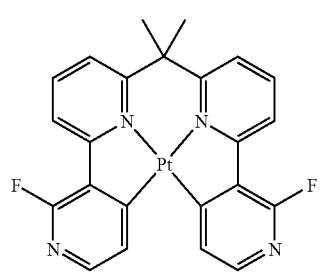

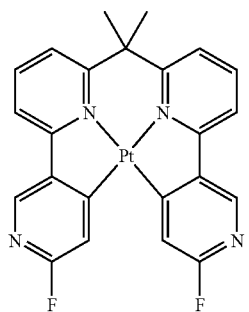
2
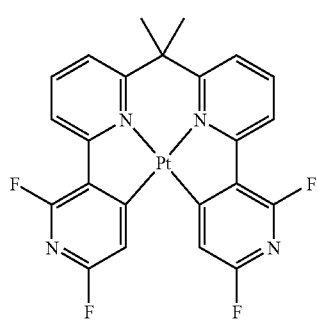
3
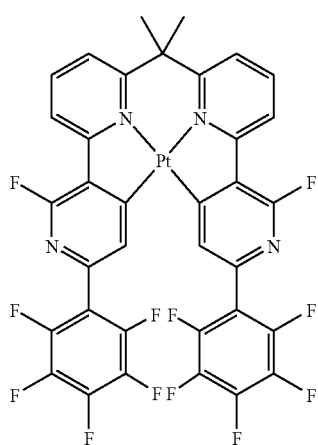
4
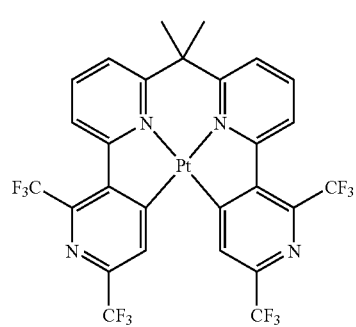
5
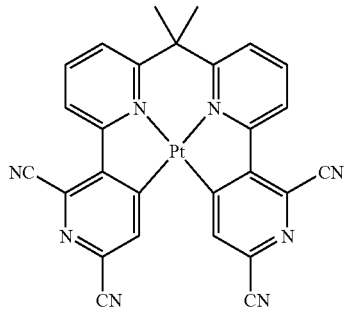
6
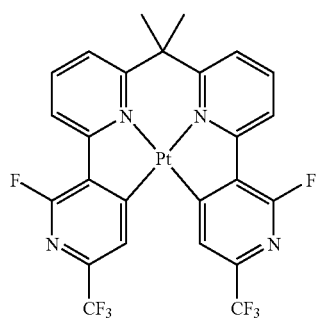
7
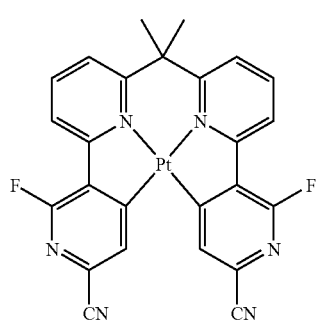
8
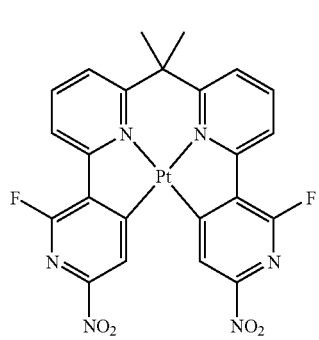
9
10

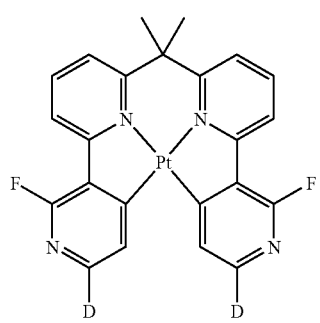
11
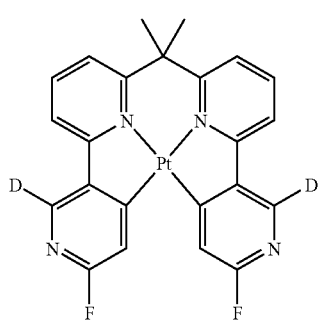
12
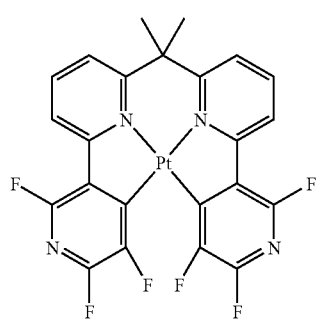
13
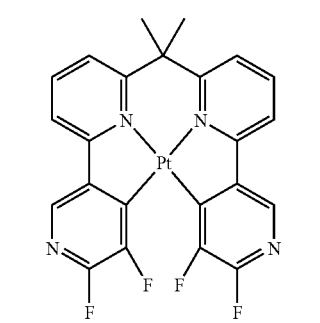
14
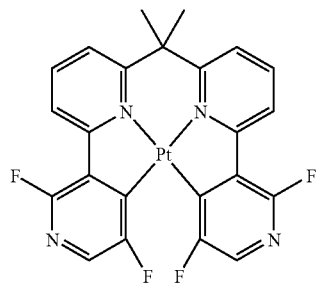
15
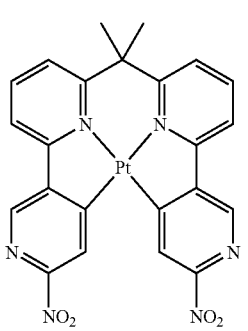
16
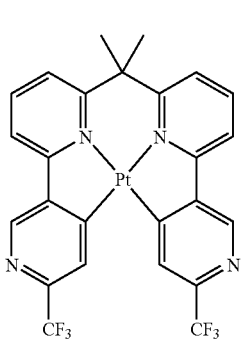
17
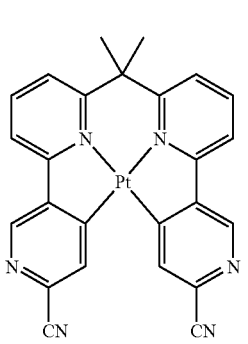
18
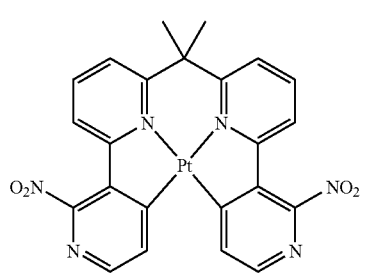
19
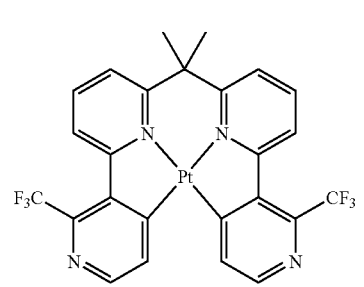
20

-continued
21
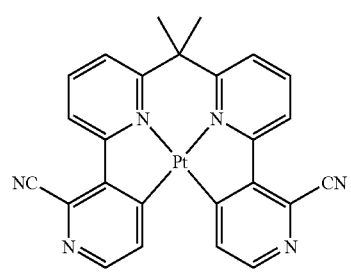
22
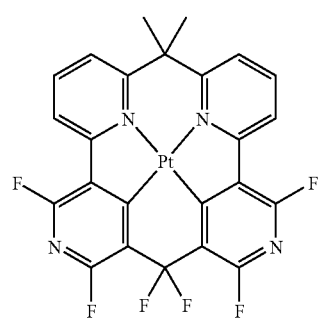
23
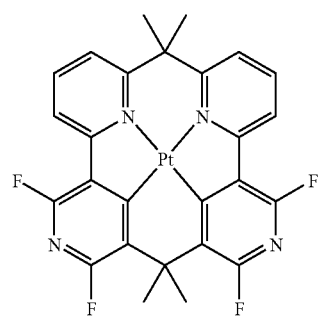
24
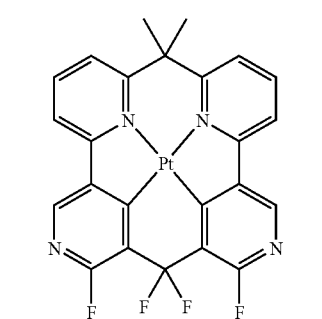
25
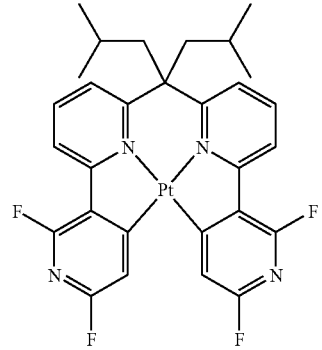
-continued
26
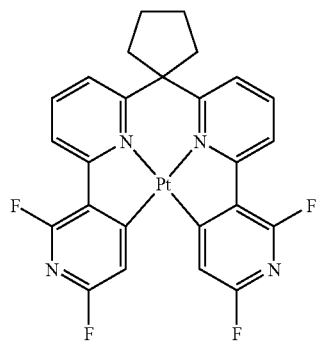
27
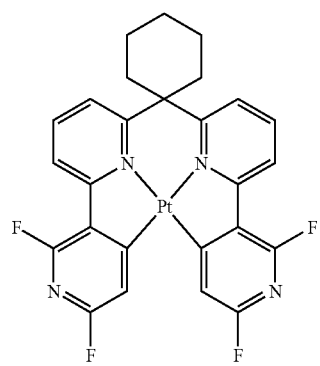
28
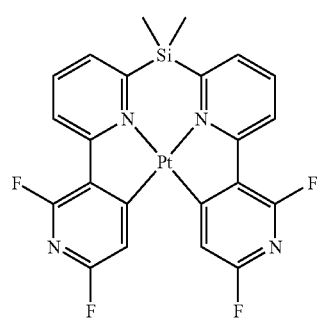
29
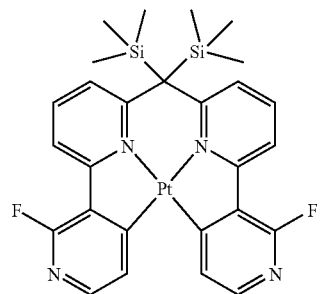
30
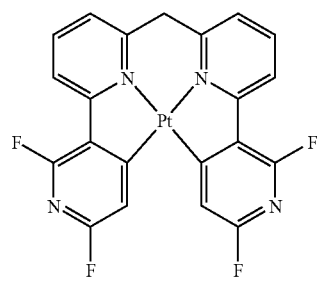

31
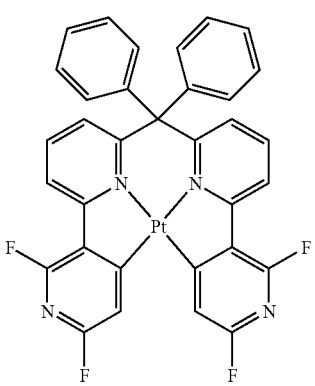
32
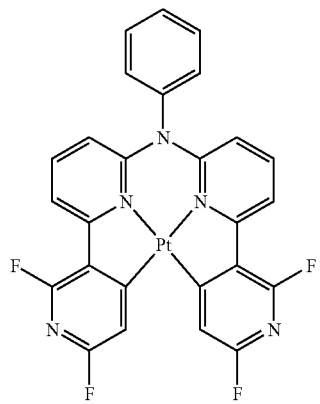
33
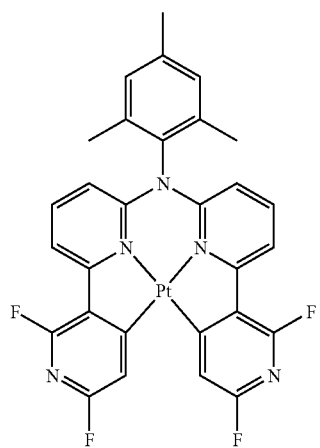
38
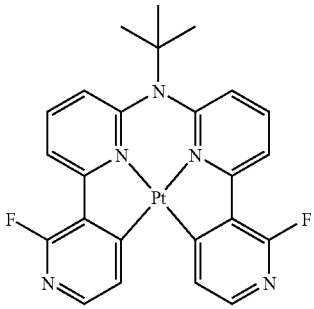
39
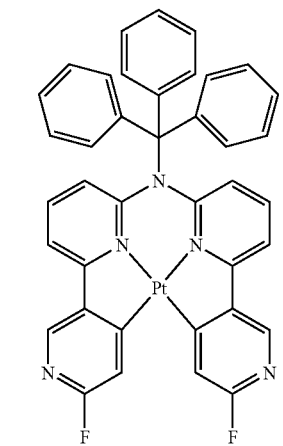
40
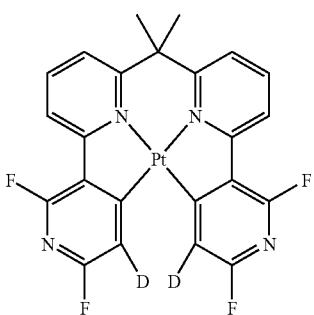
41
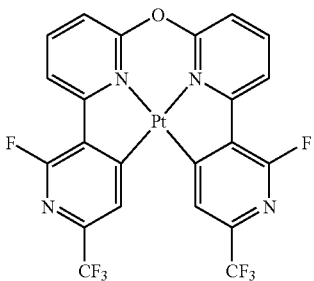

42
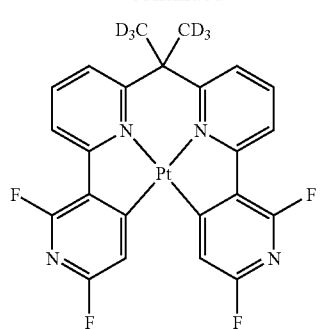
43
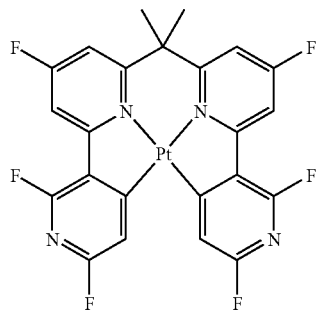
44
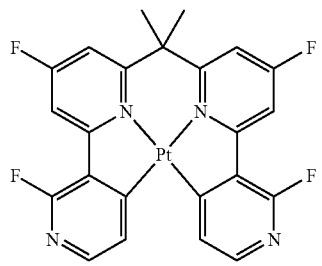
45
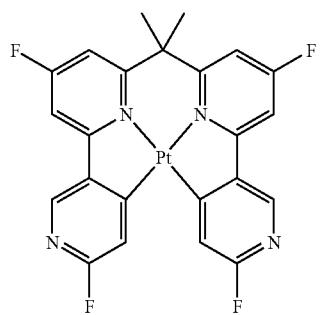
46
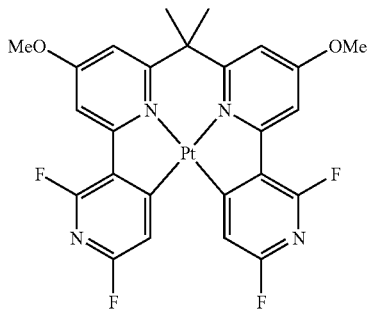
47
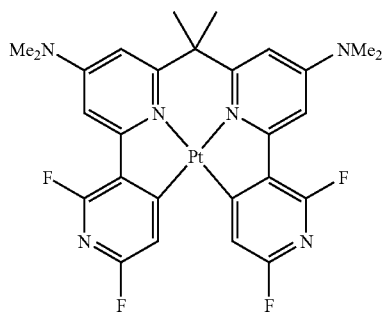
48
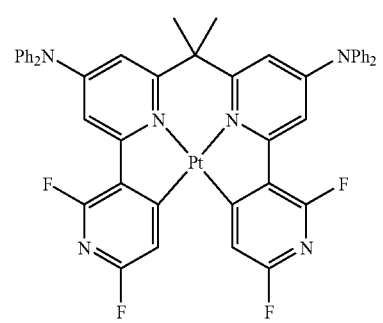
49
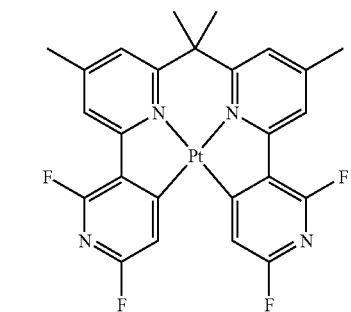
50
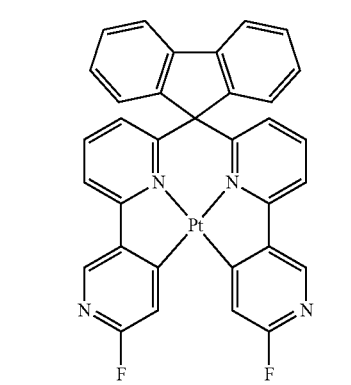
51
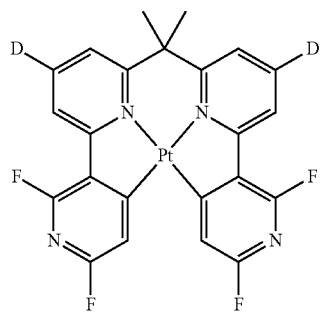

52
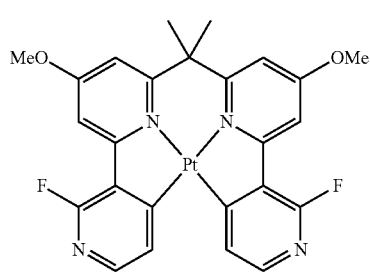
53
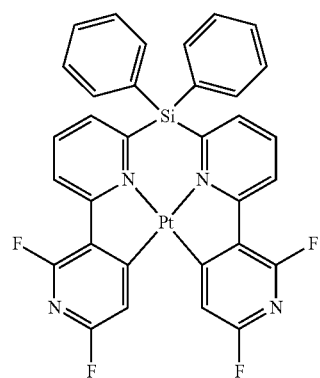
54
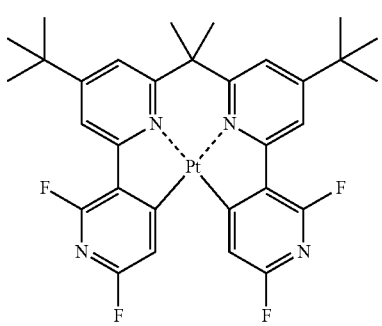
55
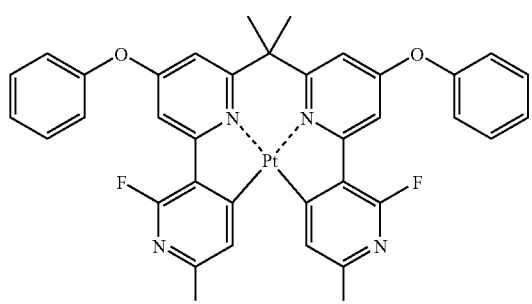
56
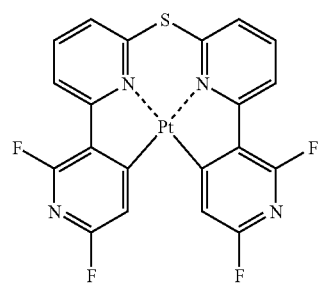
57
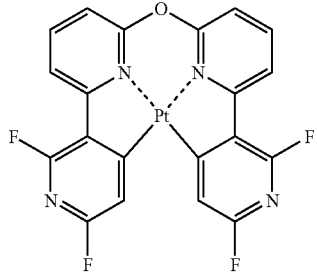
58
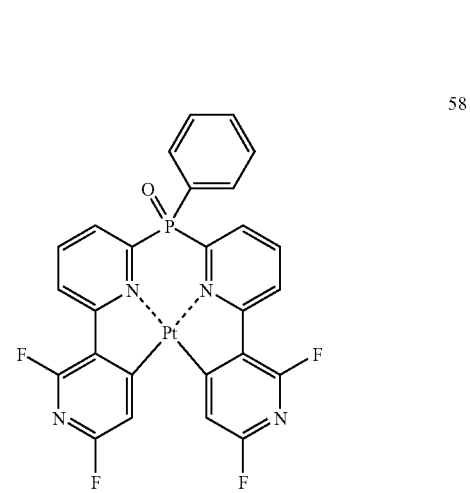
59
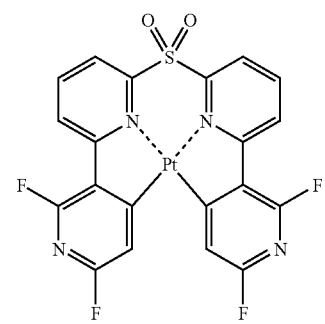
60
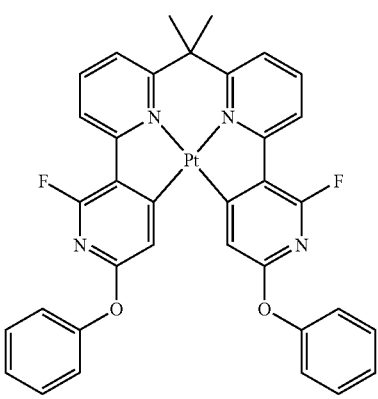

61
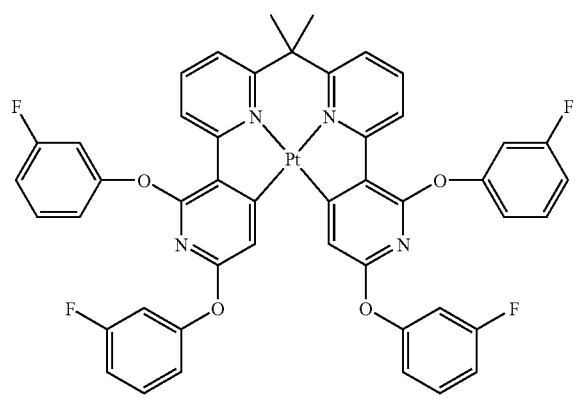
62
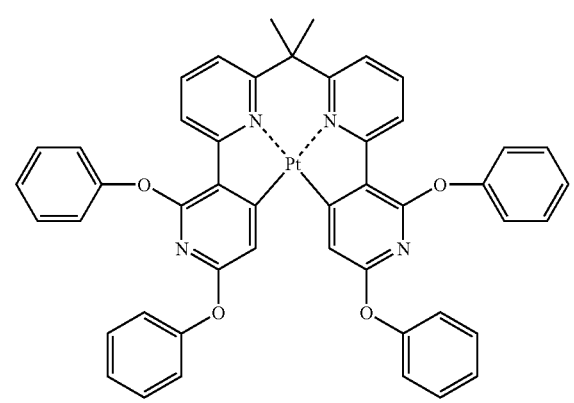
63
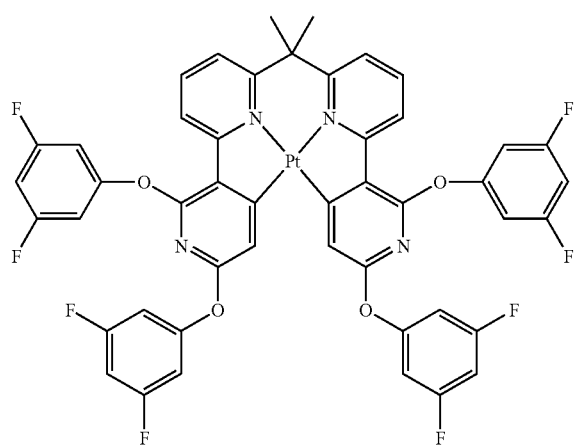
64
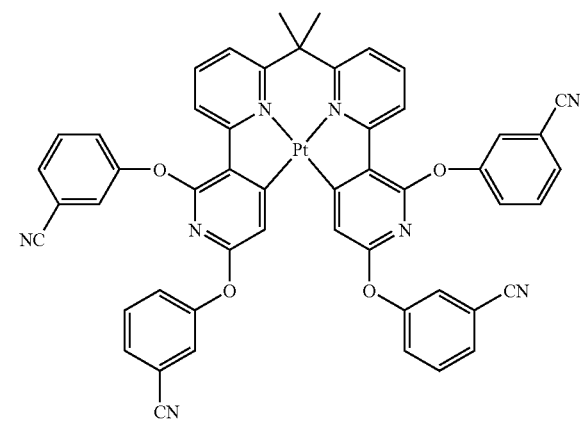
65
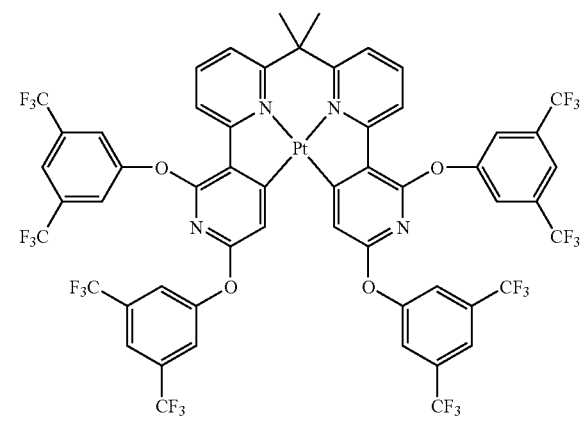
66
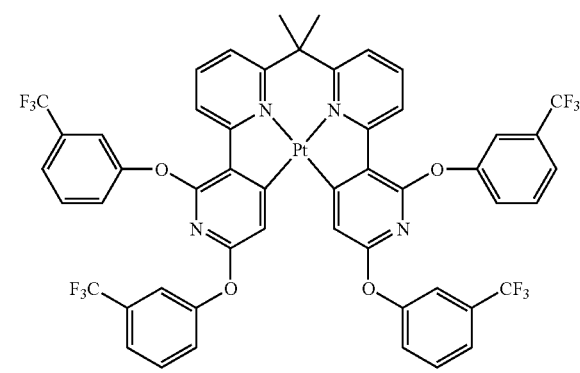
67
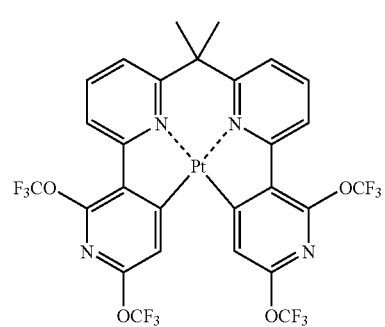

68
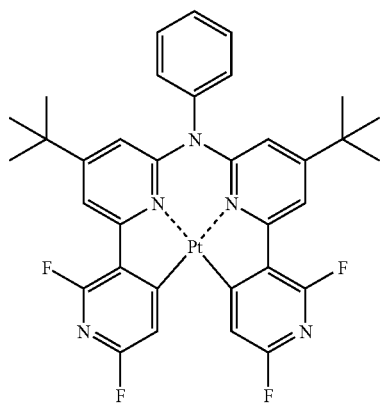
69
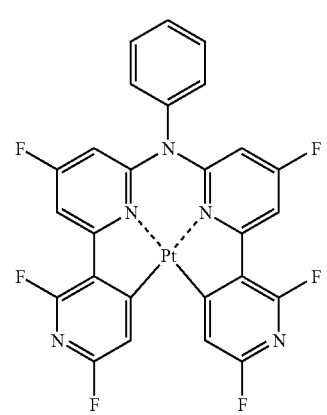
70
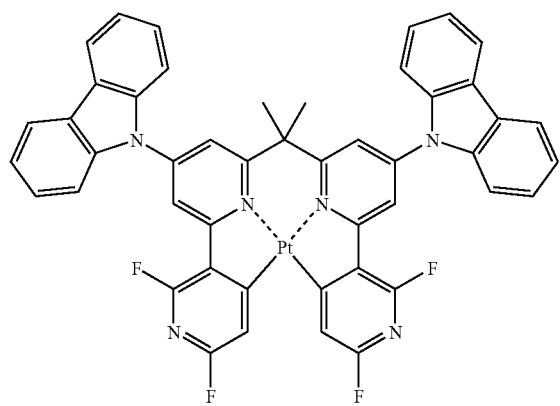
71
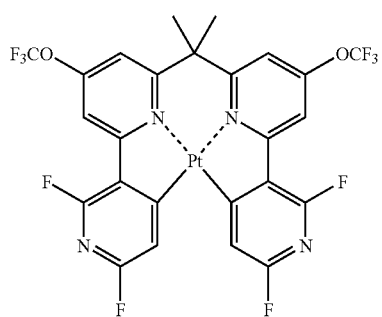
72
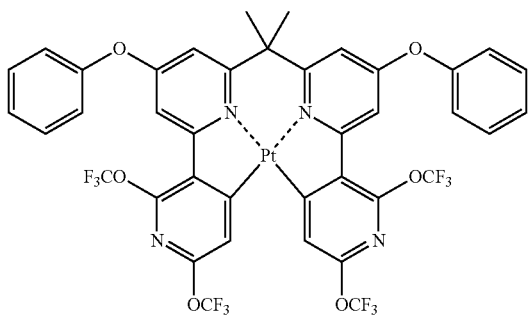
73
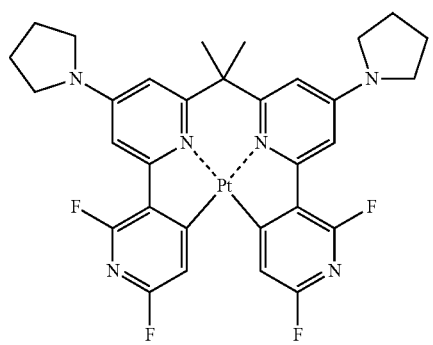
74
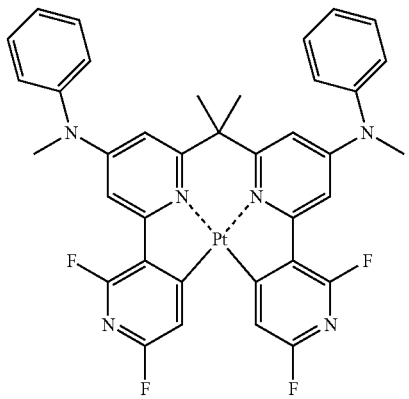
75
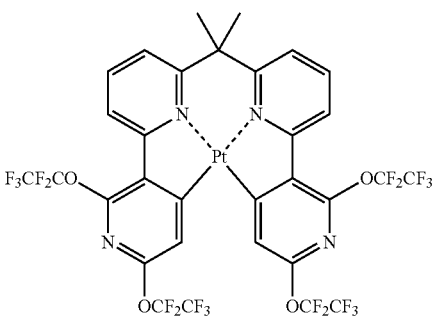

76
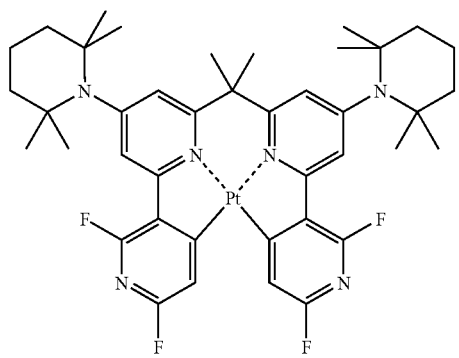
77
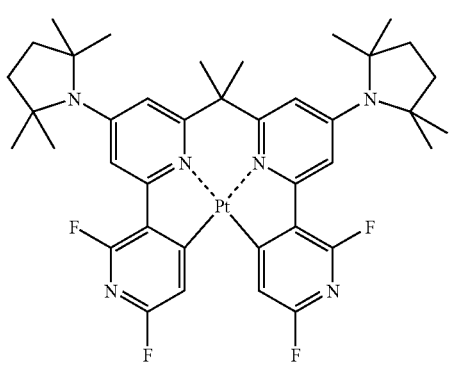
78
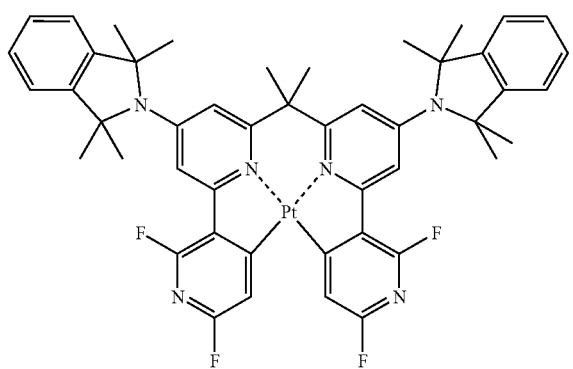
79
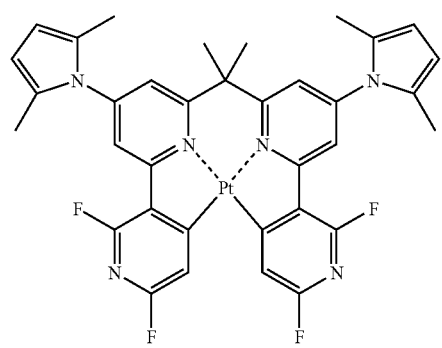
80
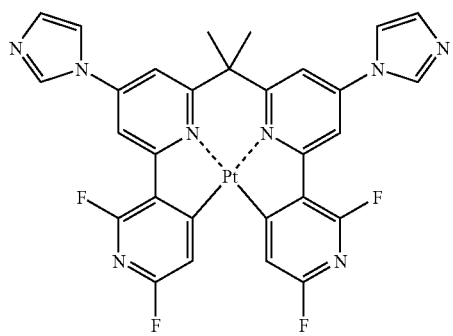
81
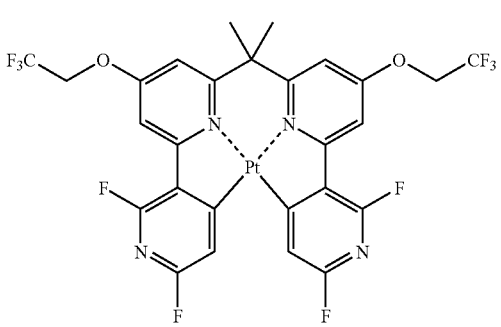
82
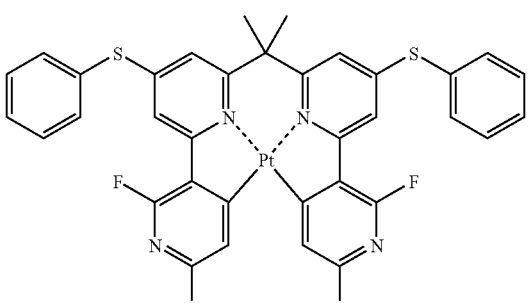
83
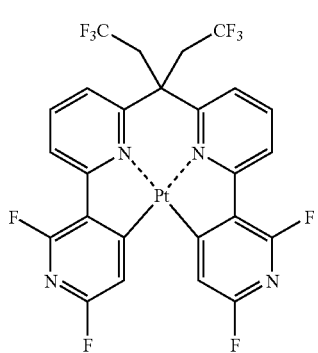
84
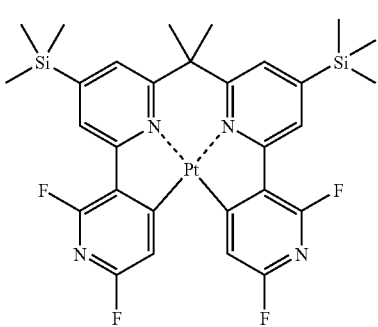

85
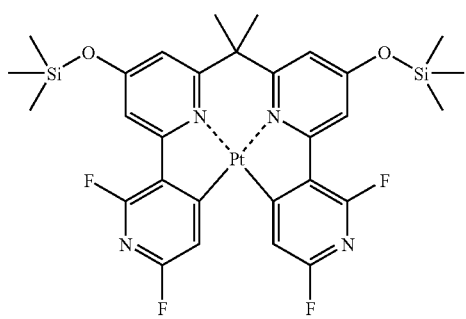
86
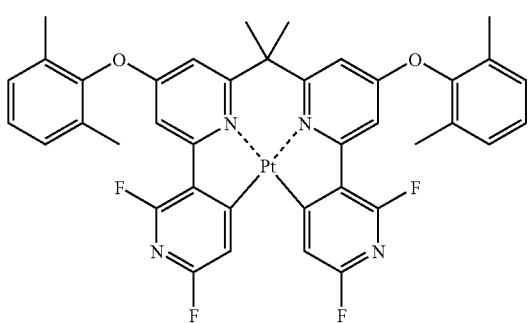
87
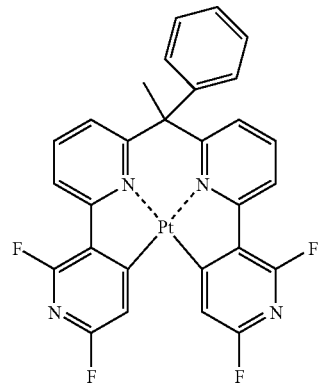
88
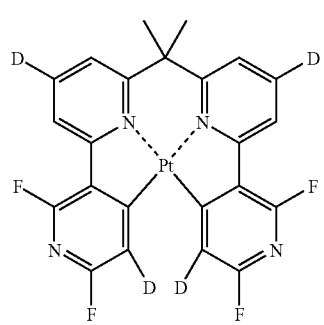
89
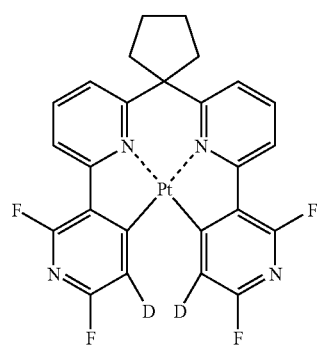
90
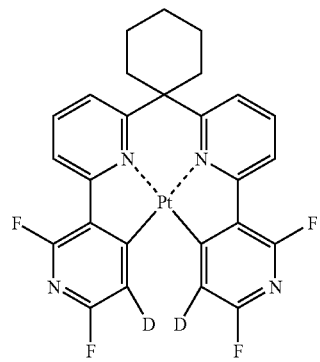
91
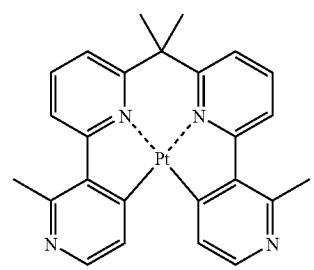
92
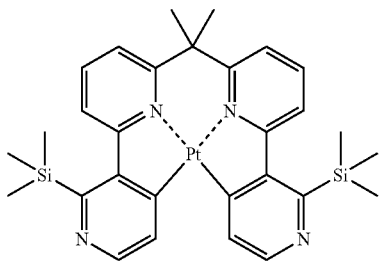
93
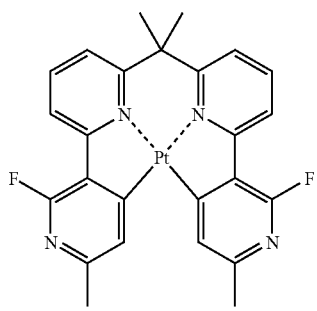

94

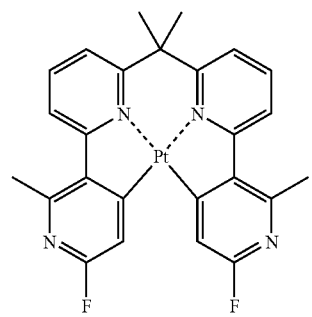

95

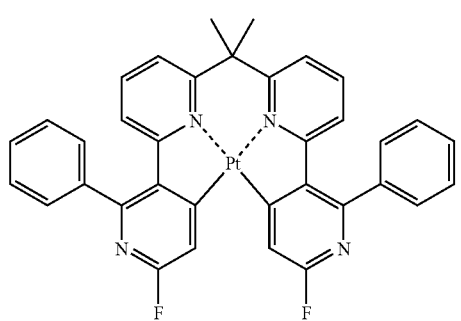

96

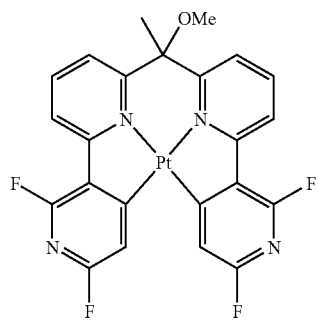

97

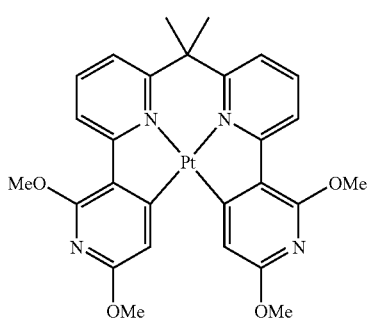

98

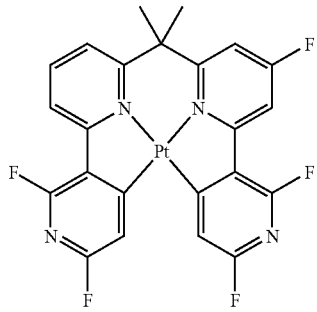

99

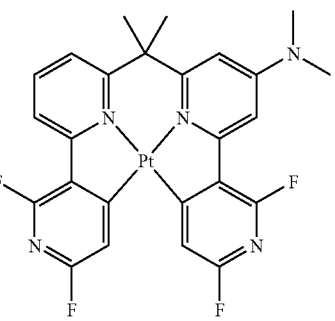

100

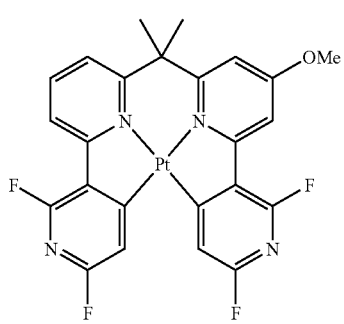

101

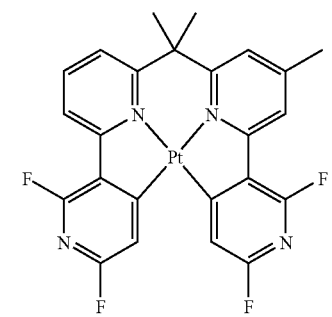

The preparation process of the invention will hereinafter be described.

The preparation process of a platinum complex represented by the formula (1) comprises reacting respective compounds represented by the formulas (B-2) and (B-2') and having a substituent at a specific position of a pyridine ring (α-position relative to the nitrogen atom of the pyridine) with a compound represented by the formula (A-0) to yield a compound represented by the formula (C-0); and reacting the compound represented by the formula (C-0) with a platinum salt.

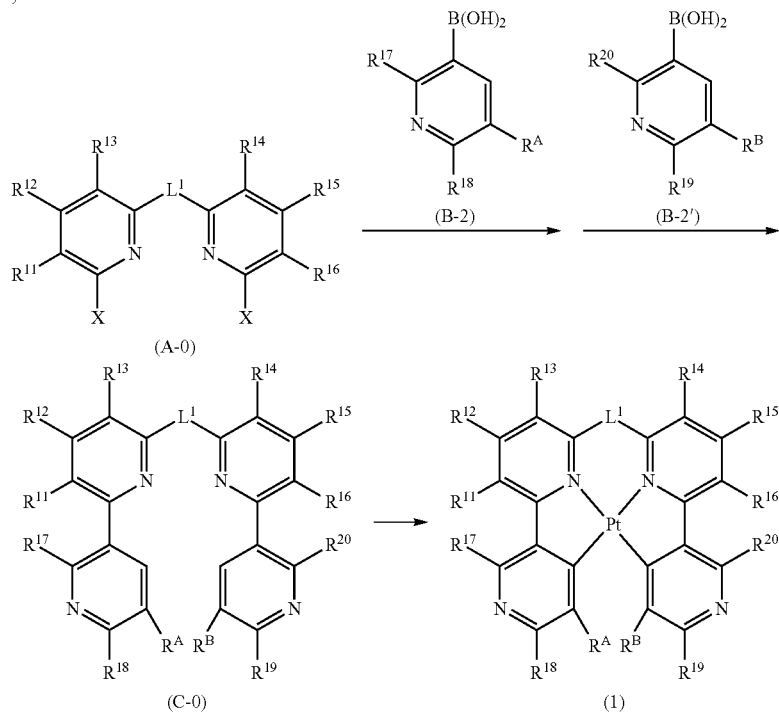

(A-0) (C-0) (1)

In the above reaction scheme, $R^{11}$, $R^{12}$, $R^{13}$, $R^{14}$, $R^{15}$, $R^{16}$, $R^{17}$, $R^{18}$, $R^{19}$, $R^{20}$, $R^A$, $R^B$ and $L^1$ have the same meanings as defined in the formula (1). X represents a halogen atom.

The compound (B-2) having a substituent at a specific position of a pyridine ring (α-position relative to the nitrogen atom of pyridine) can be synthesized from a compound (B-3) or (B-4) via a lithionated product (described in Org. Lett., 6, 277 (2004)). The compound (B-2') can be synthesized in a similar manner.

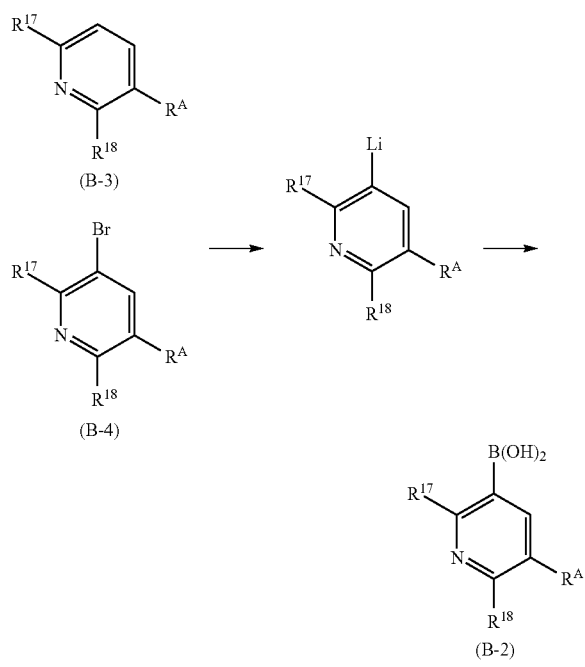

In the above reaction scheme, $R^{17}$, $R^{18}$, and $R^A$ have the same meanings as defined in the formula (1).

The compound represented by the formula (C-0) can be synthesized by reacting the compound represented by the formula (B-2) and the compound represented by the formula (B-2') with the compound represented by the formula (A-0) in a solvent in the presence of a palladium catalyst, a ligand (if necessary), and a base.

Each of the compound represented by the formula (B-2) and the compound represented by the formula (B-2') is used in an amount of from 1.0 to 10 mols, preferably from 1.0 to 6 mmols, more preferably from 1.0 to 3 mols per mol of the compound represented by the formula (A-0).

The reaction is performed typically at normal pressure, but may be performed under pressure or under reduced pressure as needed. The reaction may be performed in the air, but is performed preferably in an inert atmosphere such as nitrogen or argon in order to prevent deactivation of the palladium catalyst.

The solvent to be used for the above reaction is not particularly limited, but examples include water, aromatic hydrocarbons such as benzene, toluene, and xylene, halogenated hydrocarbons such as dichloroethane and chloroform, ethers such as tetrahydrofuran, 1,2-dimethoxyethane, 1,4-dioxane, and diethyl ether, alcohols such as methanol, ethanol, and isopropyl alcohol, and esters such as ethyl acetate and butyl acetate. Of these, water, the aromatic hydrocarbons, and the ethers are preferred. These solvents may be used either singly or in combination.

The solvent is used in an amount permitting stirring and the amount is typically from 1 to 200 times the weight, preferably from 2 to 100 times the weight, based on the weight of Compound (A-0).

For the reaction, a divalent palladium salt or a zero-valent palladium salt is used as the palladium catalyst. Examples of the divalent palladium salt include palladium acetate and dichlorobistriphenylphosphine palladium and examples of the zero-valent palladium salt include tetrakistriphenylphosphine palladium and bis(dibenzylideneacetone) palladium.

The palladium salt is used usually in an amount of from 0.0001 to 0.5 mol, preferably from 0.001 to 0.2 mol, more preferably from 0.005 to 0.1 mol per mole of Compound (A-0).

The above reaction may be performed while adding a ligand as needed. Examples of the ligand include a phosphine ligand and a carbene ligand. Of these, the phosphine ligand is preferred.

The ligand is used typically in an amount of from 0.5 to 20 mols, preferably from 1 to 10 mols, more preferably from 1 to 5 mols per mole of the palladium catalyst used for the reaction.

The base to be used in the reaction is not particularly limited and specific examples include alkali metal hydroxides such as lithium hydroxide, sodium hydroxide, and potassium hydroxide; alkaline earth metal hydroxides such as calcium hydroxide and barium hydroxide, alkali metal bicarbonates such as sodium bicarbonate and potassium bicarbonate; alkaline earth metal bicarbonates such as calcium bicarbonate and barium bicarbonate, alkali metal carbonates such as sodium carbonate and calcium carbonate, alkaline earth metal carbonates such as calcium carbonate and barium carbonate, and phosphates such as sodium phosphate and potassium phosphate. Of these, the alkali metal bicarbonates, alkali metal carbonates, and phosphates are preferred.

The base is used typically in an amount of from 0.1 to 50 mols, preferably from 1 to 20 mols, more preferably from 2 to 10 mols per mol of Compound (A-0).

The temperature of the above reaction is not particularly limited and it is typically from 0 to the boiling point of the solvent. When decomposition of the product does not occur, the reaction is performed at a temperature near the boiling point of the solvent in order to improve the reaction rate.

The platinum complex represented by the formula (1) can be obtained by reacting the compound represented by the formula (C-0) (which will hereinafter be called "ligand") with a platinum salt in the presence of a solvent.

In the preparation process of the invention, examples of a platinum salt to be used for the reaction for forming a complex between the platinum salt and the ligand and containing divalent platinum include platinum chloride, platinum bromide, platinum iodide, platinum acetylacetonate, bis(benzonitrile)dichloroplatinum, bis(acetonitrile)dichloroplatinum, dichloro(1,5-cyclooctadiene)platinum, dibromobis(triphenylphosphine)platinum, dichloro(1,10-phenanthroline)platinum, dichlorobis(triphenylphosphine)platinum, diaminedichloroplatinum, diamminediiodoplatinum, potassium tetrabromoplatinate, potassium tetrachloroplatinate, and sodium tetrachloroplatinate. Of these platinum salts, platinum chloride, bis(benzonitrile)dichloroplatinum(II) and bis(acetonitrile)dichloroplatinum(II) are preferred over the others.

These metal compounds may contain water of crystallization, a solvent of crystallization, or a coordinating solvent.

The valence of the metal is not particularly limited, but the metal is preferably divalent or zero-valent, more preferably divalent.

In the preparation process of the invention, an amount of the platinum salt to be used for the complex forming reaction between the platinum salt and the ligand is, when the platinum salt contains one platinum atom for forming the corresponding complex, typically from 0.1 to 10 mols, preferably from 0.5 to 5 mols, still more preferably from 1 to 3 mols per mole of the ligand. When the platinum salt contains n pieces of platinum atoms for forming the corresponding complex, the amount may be 1/n mol.

Examples of a solvent used at the time of complexation reaction between a platinum salt and a ligand in the present preparation process include amides such as N,N-dimethylformamide, formamide and N,N-dimethylacetamide, nitrites such as acetonitrile, propionitrile, butyronitrile and benzonitrile, halogenated hydrocarbons such as dichloromethane, 1,2-dichloroethane, chloroform, carbon tetrachloride, chlorobenzene and o-dichlorobenzene, aliphatic hydrocarbons such as pentane, hexane, octane and decane, aromatic hydrocarbons such as benzene, toluene, xylene and mesitylene, ethers such as diethyl ether, diisopropyl ether, butyl ether, tert-butyl methyl ether, 1,2-dimethoxyethane, tetrahydrofuran and 1,4-dioxane, ketones such as acetone, methyl ethyl ketone and methyl isobutyl ketone, alcohol compounds such as methanol, ethanol, 1-propanol, 2-propanol, tert-butyl alcohol, 2-methoxyethanol, 2-ethoxyethanol, ethylene glycol and glycerin, carboxylic acids such as acetic acid and propionic acid, and water. Of these solvents, nitriles such as acetonitrile, propionitrile, butyronitrile and benzonitrile, and aromatic hydrocarbons such as benzene, toluene, xylene and mesitylene are especially preferable to the others. These solvents may be used alone or as mixtures of two or more thereof.

In the preparation process of the invention, an amount of the solvent to be used for the complex forming reaction between the platinum salt and the ligand is not particular limited insofar as it permits adequate progress of the reaction. It is used in an amount of typically from 1 to 200 times the volume, preferably from 5 to 100 times the volume of the ligand used in the reaction.

In the preparation process of the invention, when an acid substance such as halogenated hydrogen is formed during the complex forming reaction between the platinum salt and the ligand, the reaction may be performed in the presence of a basic substance. Examples of the basic substance include tertiary amines such as triethylamine, diisopropylethylamine, and pyridine, metal alkoxides such as sodium methoxide and sodium ethoxide, and inorganic bases such as sodium hydroxide, potassium hydroxide, potassium carbonate, and sodium bicarbonate. Alternatively, an acid substance, such as hydrogen halogenide, produced at the time of complexation can be removed from the reaction solution or reduced in its content in the reaction solution by blowing an inert gas, such as nitrogen or argon, into the reaction solution.

In the preparation process of the invention, the complex forming reaction between the platinum salt and the ligand is performed preferably in an inert gas atmosphere. Examples of the inert gas include nitrogen and argon.

The reaction temperature, the reaction time, and reaction pressure in the complex forming reaction between the platinum salt and the ligand in the preparation process of the invention each differs, depending on the raw material or the solvent. The reaction temperature is typically from 20 to 300° C., preferably from 50 to 250° C., still more preferably from 80 to 220° C.; the reaction time is typically from 30 minutes to 24 hours, preferably from 1 to 12 hours, more preferably from 2 to 10 hours; and the reaction pressure is typically normal pressure, but may be under pressure or under reduced pressure as needed.

In the preparation process of the invention, a heating unit to be used in the complex forming reaction between the platinum salt and the ligand is not limited. For example, heating over an oil bath, heating in a mantle heater, or heating by exposure to microwaves can be employed.

A preparation process of a compound represented by the following formula (D-1) which is the complex of the invention will next be described specifically.

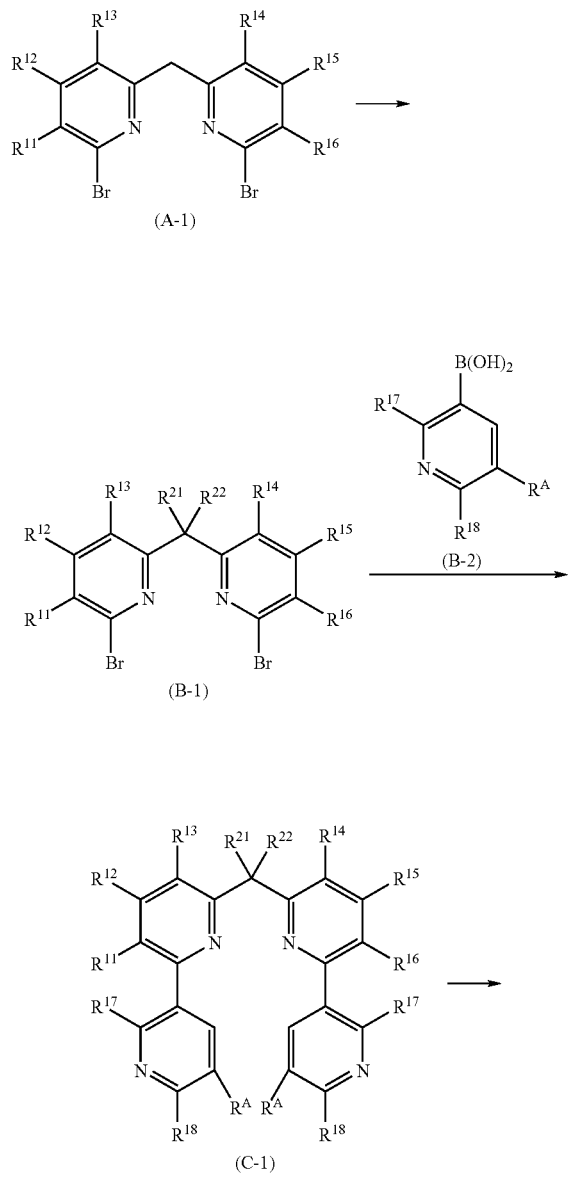

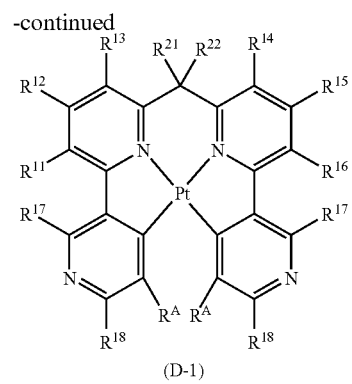

wherein, $R^{11}$, $R^{12}$, $R^{13}$, $R^{14}$, $R^{15}$, $R^{16}$, $R^{17}$, $R^{18}$, $R^{21}$, $R^{22}$ and $R^A$ have the same meanings as defined in the formula (2).

The complex of the invention can be obtained by the process described on page 789, from line 53 on left column to line 7 on right column, of *Journal of Organic Chemistry*, 53, 786 (1988), by G. R. Newkcome, et al. or the process described on page 790, from line 18 to line 38 on left column, and from line 19 to line 30 on right column, of the same literature, or combination of them. Compound (A-1) is used as a starting substance. To an N,N-dimethylformamide solution of Compound (A-1) is added from 1 to 1.2 equivalents of a base such as lithium diisopropylamide, potassium t-butoxide, or sodium hydride at from 0° C. to room temperature. The resulting mixture is reacted for about 30 minutes at from 0° C. to room temperature. To the reaction mixture is added from 1.5 to 4 equivalents of an alkyl halide represented by $R^{21}X$ ($R^{21}$ has the same meaning as defined above in the formula (2) and X represents a halogen atom) and the mixture is reacted for about 30 minutes at room temperature to obtain the corresponding monoalkyl. Under the similar conditions, from 1 to 1.2 equivalents of the base is reacted with an excess amount of an alkyl halide $R^{22}X$ ($R^{22}$ has the same meaning as defined above in the formula (2) and X represents a halogen atom), whereby a dialkyl-substituted compound (B-1) can be obtained in a yield of from 70 to 99%. The compound (B-1) having a cyclopentane ring can be synthesized by using 1,4-dibromobutane or the like as the alkyl halide, while the compound (B-1) having a cyclohexane ring can be synthesized by using 1,5-dibromopentane or the like as the alkyl halide, An intended compound can be synthesized by using the process as described in *Synth. Commun.*, 11, 513 (1981) as a step for obtaining Compound (C-1) from Compound (B-1).

Compound (D-1) of the invention can be obtained from Compound (C-1) in the following manner. It can be synthesized by dissolving Compound (C-1) and from 1 to 1.5 equivalents of platinum chloride in benzonitrile, heating the resulting solution to from 130° C. to reflux temperature (boiling point of benzonitrile: 191° C.), and stirring the reaction mixture for from 30 minutes to 4 hours. Compound (D-1) can be purified by recrystallization from chloroform or ethyl acetate, silica gel column chromatography, or sublimation.

Of the platinum complexes of the invention, a complex represented by the following formula (H-1) can be synthesized by the following preparation process.

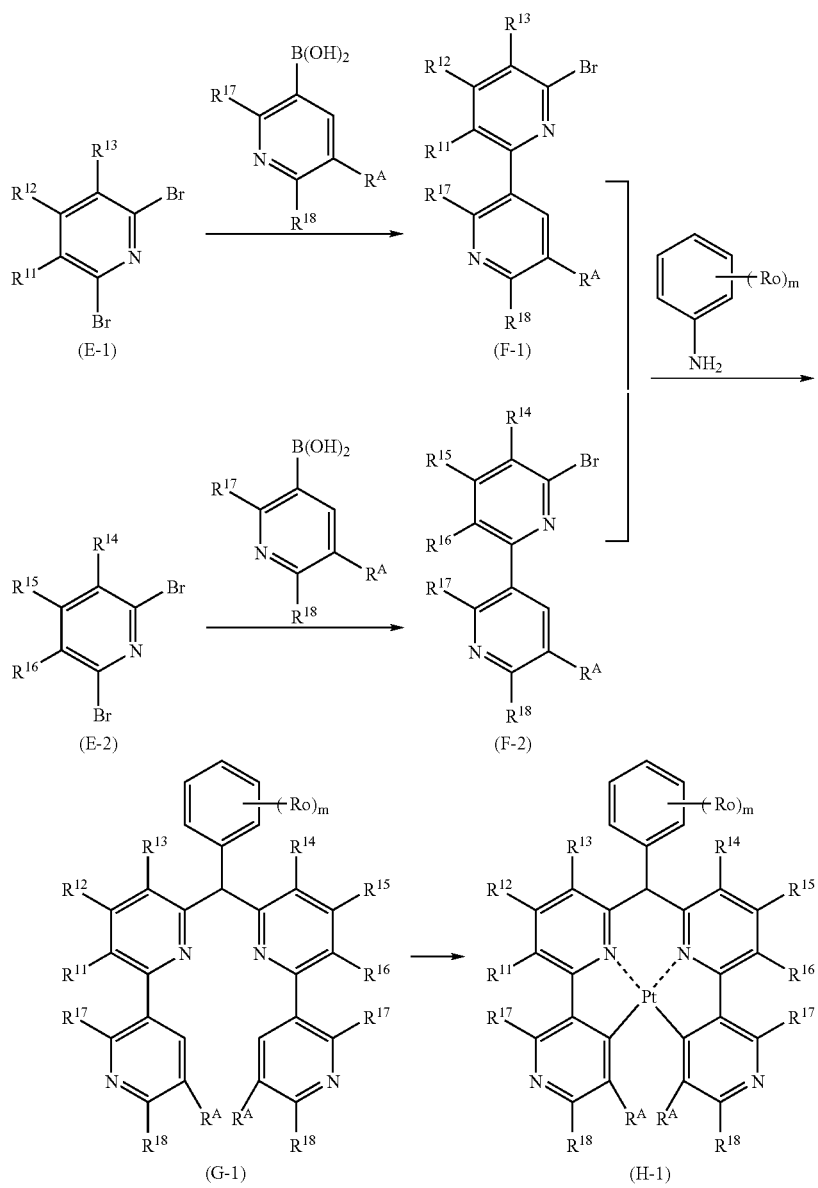

In the above reaction scheme, $R^{11}$, $R^{12}$, $R^{13}$, $R^{14}$, $R^{15}$, $R^{16}$, $R^{17}$, $R^{18}$ and $R^A$ have the same meanings as defined in the formula (2); Ro represents a substituent selected from Substituent Group B, and m stands for an integer of from 0 to 5.

An intended compound can be synthesized using the process as described in *Synth. Commun.*, 11, 513 (1981) as a step for obtaining Compound (F-1) from Compound (E-1) or a step for obtaining Compound (F-2) from Compound (E-2).

An intended compound can be synthesized using the process as described in *Angew. Chem. Int. Ed.*, 42, 2051-2053 (2003) as a step for obtaining Compound (G-1) from Compound (F-1) or Compound (F-2).

Compound (H-1) of the invention can be obtained from Compound (G-1) by dissolving Compound (G-1) and from 1 to 1.5 equivalents of platinum chloride in benzonitrile, heating the resulting solution to from 130° C. to reflux temperature (the boiling point of benzonitrile: 191° C.), and stirring the reaction mixture for from 30 minutes to 4 hours. Compound (H-1) can be purified by recrystallization from chloroform or ethyl acetate, silica gel column chromatography, or sublimation.

In the above-described preparation process, when the substituent defined changes under certain conditions of the synthesis process or is not suited for enforcing the process, it is possible to prepare the intended compound easily, for example, by protecting or deprotecting a functional group (for example, *Protective Groups in Organic Synthesis*, written by T. W. Greene, published by John Wiley & Sons, Inc. in 1981). If necessary, the order of the reaction steps such as introduction of a substituent can be changed as needed.

The device of the invention will hereinafter be described in detail.

The device of the invention is an organic electroluminescence device having a pair of electrodes and one or more organic layers therebetween, wherein at least one of the platinum complexes of the invention is contained in the one or more organic layers. When the device has one organic layer, it has a light emitting layer as the organic layer. At least one of electrodes, that is, anode and cathode is preferably transparent or semi-transparent judging from the nature of the device.

The device of the invention is characterized by that the one or more organic layers of it contain a complex having a tetradentate ligand with a specific structure. The organic layers are not particularly limited, but the device may have, in addition to the light emitting layer, a hole injection layer, a hole transport layer, an electron injection layer, an electron transport layer, a hole blocking layer, an electron blocking layer, an exciton blocking layer, and a protective layer. Each of these layers may have another function, simultaneously.

As a stack mode of the organic layers in the invention, a mode in which a hole transport layer, a light emitting layer, and an electron transport layer are stacked successively from the side of the anode is preferred. Further, the device may have a charge blocking layer between the hole transport layer and the light emitting layer or between the light emitting layer and the electron transport layer. The device may have the hole injection layer between the anode and the hole transport layer. Similarly, it may have an electron injection layer between the cathode and the electron transport layer. Each layer may be divided into a plurality of secondary layers.

When the device has two or more organic layers, the complex of the invention can be contained in any of these layers. The complex of the invention is preferably contained in the light emitting layer, more preferably contained in the light emitting layer as a light emitting material or a host material, still more preferably contained in the light emitting layer as a light emitting material, especially preferably contained in the light emitting layer together with at least one host material.

When the complex of the invention is introduced into a layer (for example, an electron transport layer) other than the light emitting layer, it is contained in the layer preferably in an amount of from 10 to 100 mass %, more preferably from 30 to 100 mass %.

Each element constituting the device of the invention will be described specifically.

<Substrate>

The substrate to be used in the invention preferably does not scatter or attenuate light emitted from the organic layers. Specific examples include inorganic materials such as yttria-stabilized zirconium (YSZ) and glass; and organic materials, e.g., polyesters such as polyethylene terephthalate, polybutylene terephthalate, and polyethylene naphthalate, polystyrenes, polycarbonates, polyethersulfones, polyarylates, polyimides, polycycloolefins, norbornene resins, and poly (chlorotrifluoroethylene).

For example, when glass is used as the substrate, use of an alkali-free glass is preferred in order to minimize elution of ions from the glass. When soda lime glass is used, a barrier coated one with, for example, silica is preferred. Substrates made of the organic materials are preferred because they are excellent in heat resistance, dimensional stability, solvent resistance, electrical insulating properties, and processability.

The shape, structure, and size of the substrate are not particularly limited and can be selected as needed according to the intended use or purpose of the luminescence device. In general, the substrate is preferably in the form of a plate and may have either a single layer structure or a stacked structure. It may be made of a single member or two or more members.

Although the substrate may be either colorless and transparent or colored and transparent, a colorless and transparent substrate is preferred because such a substrate causes neither scattering nor attenuation of light emitted from the organic light emitting layer.

The substrate can have, on the surface or backside surface thereof, a moisture penetration preventing layer (gas barrier layer).

As materials for the moisture penetration preventing layer (gas barrier layer), inorganic substances such as silicon nitride and silicon oxide are suited. The moisture penetration preventing layer (gas barrier layer) can be formed, for example, by RF sputtering.

When a thermoplastic substrate is used, it may have a hard coat layer or an undercoat layer further if necessary.

<Anode>

The anode is usually not particularly limited in shape, structure, or size insofar as it has a function as an electrode supplying holes to the organic layers. Materials of the anode can be selected as needed from known electrode materials, depending on the intended use or purpose of the luminescence device. As described above, the anode is usually formed as a transparent anode.

Examples of the materials of the anode include metals, alloys, metal oxides, and electroconductive compounds, and mixtures thereof. Specific examples of the anode material include electroconductive metal oxides such as tin oxides doped with antimony and fluorine (e.g., ATO and FTO), tin oxide, zinc oxide, indium oxide, indium tin oxide (ITO) and indium zinc oxide (IZO), metals such as gold, silver, chromium, and nickel, mixtures or stacks of these metals and electroconductive metal oxides; inorganic electroconductive substances such as copper iodide and copper sulfide, organic electroconductive materials such as polyaniline, polythiophene, and polypyrrole; and stacks of these materials with ITO. Among these materials, electroconductive metal oxides are preferred, with ITO being especially preferred from the viewpoint of productivity, and high conductivity, transparency.

The anode can be formed over the substrate by a process selected as needed from the wet processes such as printing and coating, physical processes such as vacuum deposition, sputtering and ion plating, and chemical processes such as CVD and plasma CVD in consideration of its suitability to the material constituting the anode. When ITO is selected as the anode material, the anode can be formed by DC sputtering, RF sputtering, vacuum deposition, or ion plating.

In the organic electroluminescence device of the invention, the formation position of the anode is not particularly limited and it can be selected as needed depending on the intended use or purpose of the luminescence device. It is however preferably formed on the substrate. In this case, the anode may be formed all over the one surface of the substrate or may be formed in a part thereof.

When the anode is formed, patterning may be performed by chemical etching using photolithography or physical etching with laser exposure. The anode may also be formed by vacuum deposition or sputtering through stacked masks, a lift-off process, or a printing process.

Although the thickness of the anode can be selected as needed, depending on the material constituting the anode and it cannot be specified in a wholesale manner, the thickness is usually from approximately 10 nm to 50 μm, preferably from 50 nm to 20 μm.

The resistivity of the anode is preferably $10^3$ Ω/sq or less, more preferably $10^2$ Ω/sq. The anode may be either colorless or colored insofar as it is transparent. The transmittance of the anode is preferably 60% or greater, more preferably 70% or greater in order to obtain luminescence from the side of the transparent anode.

Detailed description on transparent anodes is given in *Development of Transparent Conductive Films*, supervised by Yutaka Sawada, published by CMC (1999) and it can be applied to the invention. When a plastic base material having low heat resistance is used, a transparent anode formed using ITO or IZO at a temperature as low as 150° C. or less is preferred.

<Cathode>

The shape, structure or size of the cathode is usually not particularly limited insofar as it has a function as an electrode charging electrons into the organic layers. The material of it can be selected as needed from known electrode materials, depending on the intended use or purpose of the luminescence device.

Materials making up the cathode are, for example, metals, alloys, metal oxides, and electroconductive compounds, and mixtures thereof. Specific examples include alkali metals (such as Li, Na, K, and Cs), alkaline earth metals (such as Mg and Ca), gold, silver, lead, aluminum, sodium-potassium alloy, lithium-aluminum alloy, magnesium-silver alloy, and rare earth metals such as indium and ytterbium. These materials may be used alone. From the viewpoint of satisfying both stability and electron injection property, however, two or more of them can be used preferably in combination.

Of theses alkali metals and alkaline earth metals are preferred as the material constituting the cathode from the viewpoint of electron injection property, while materials composed mainly of aluminum are preferred because of their excellent storage stability.

The term "materials composed mainly of aluminum" means a single substance of aluminum and mixtures or alloys composed of aluminum and from 0.01 to 10 mass % of an alkali metal or an alkaline earth metal (such as a lithium-aluminum alloy and a magnesium-aluminum alloy).

The materials of the cathode are described in detail in JP-A-2-15595 and JP-A-5-121172 and the materials described therein can also be employed in the invention.

The process of forming the cathode is not particularly limited and it can be formed in a known manner. It can be formed in accordance with a process selected as needed from wet processes such as printing and coating, physical processes such as vacuum deposition, sputtering and ion plating, and chemical processes such as CVD and plasma CVD in consideration of the suitability to the above-described material making up the cathode. When a metal is selected as the material for the cathode, the cathode may be formed by simultaneously or successively sputtering one or more of the metals.

When the cathode is formed, patterning may be performed by chemical etching using photolithography or physical etching with laser exposure. The cathode may also be formed by vacuum deposition or sputtering through stacked masks, or by a lift-off process or a printing process.

In the invention, the forming position of the cathode is not particularly limited and it may be formed all over the organic layer or may be formed over a part thereof.

A dielectric layer made of, for example, a fluoride or oxide of an alkali metal or an alkaline earth metal and having a thickness of from 0.1 nm to 5 nm may be inserted between the cathode and the organic layer. This dielectric layer can also be regarded as a kind of an electron injection layer. It may be formed, for example, by vacuum deposition, sputtering or ion plating.

The thickness of the cathode can be selected as needed, depending on the material constituting the cathode and it cannot be determined in a wholesale manner. The thickness is usually from 10 nm to 5 μm, preferably from 50 nm to 1 μm.

The cathode may be either transparent or opaque. A transparent cathode can be obtained by forming the material of the cathode into a thin film with a thickness of from 1 to 10 nm and then stacking thereover a transparent conductive material such as ITO or IZO.

<Organic Layer>

The organic layer of the invention will next be described. The device of the invention contains one or more organic layers including the light emitting layer. Examples of the organic layer other than the organic light emitting layer include, as described above, a hole transport layer, an electron transport layer, a hole blocking layer, an electron blocking layer, a hole injection layer, and an electron injection layer.

-Formation of Organic Layer-

Each layer constituting the one or more organic layers of the organic electroluminescence device of the invention can be formed preferably by any one of dry film forming processes such as vapor deposition or sputtering, transfer process and printing process.

-Light Emitting Layer-

The light emitting layer is a layer having a function of, when voltage is applied, receiving holes from the anode, the hole injection layer, or the hole transport layer, receiving electrons from the cathode, the electron injection layer, or the electron transport layer, and providing a recombination site of the holes and the electrons to cause light emission.

The light emitting layer in the invention may be composed only of a. light emitting material. Alternatively, it may be composed of a mixed layer of a host material and a light emitting material. As the light emitting layer, that using the complex of the invention as the light emitting material and the host material is preferred.

The light emitting layer may be either a single layer or a combination of two or more layers. In the latter case, these layers may emit lights of different colors.

The suitable thickness of the light emitting layer, though not particular limited, is generally from 1 nm to 500 nm, preferably from 5 nm to 200 nm, more preferably from 10 nm to 100 nm.

<Light Emitting Material>

The light emitting material may be either a fluorescent material or phosphorescent material. Only one kind of light emitting material may be used, or two or more kinds of light emitting materials may be used.

The light emitting layer used in the invention can contain two or more kinds of light emitting materials for the purposes of enhancing the color purity and extending a wavelength range of light emission.

(Fluorescent Material)

Examples of the fluorescent material usable in the invention include benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, aromatic fused compounds, perinone derivatives, oxadiazole derivatives, oxazine derivatives, aldazine derivatives, pyralidine derivatives, cyclopentadiene derivatives, bis(styryl)anthracene derivatives, quinacridone derivatives, pyrrolopyridine derivatives, thiadiazolopyridine derivatives, cyclopentadiene derivatives, styrylamine derivatives, diketopyrrolopyrrole derivatives, aromatic dimethylidyne compounds, various complexes as typified by complexes of 8-quinolynol and complexes of a pyrromethene derivative, polymer compounds such as polythiophene, polyphenylene, and polyphenylene vinylene, and organosilane derivatives.

(Phosphorescent Material)

Examples of the phosphorescent material usable in the invention include phosphorescent compounds as described in patent documents such as U.S. Pat. Nos. 6,303,238B1 and 6,097,147, WO 00/57676, 00/70655, 01/08230, 01/39234A2, 01/41512A1, 02/02714A2, 02/15645A1, 02/44189A1, and 05/19373A2, and JP-A-2001-247859, JP-A-2002-302671, JP-A-2002-117978, JP-A-2003-133074, JP-A-2002-235076, JP-A-2003-123982, JP-A-2002-170684, EP1211257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635, and JP-A-2007-96259. Of these, more preferred examples of the luminescent dopants include Ir complexes, Pt complexes, Cu complexes, Re complexes, W complexes, Rh complexes, Ru complexes, Pd complexes, Os complexes, Eu complexes, Tb complexes, Gd complexes, Dy complexes, and Ce complexes, of which Ir complexes, Pt complexes, and Re complexes are especially preferred. Of these, Ir complexes, Pt complexes, and Re complexes each containing at least one coordination mode of a metal-carbon bond, a metal-nitrogen bond, a metal-oxygen bond, and a metal-sulfur bond are preferred. Furthermore, from the standpoint of luminous efficiency, running durability, and chromaticity, Ir complexes, Pt complexes and Re complexes each containing a tridentate or higher-dentate ligand are especially preferred.

The content of phosphorescent materials usable in the invention (the present complexes and/or phosphorescent materials used in combination) is preferably from 0.1 mass % to 60 mass %, more preferably from 0.2 mass % to 50 mass %, still more preferably from 0.3 mass % to 40 mass %, especially preferably from 0.5 mass % to 30 mass %, with respect to the total mass of the light emitting layer.

When the present complexes are used in combination with other phosphorescent materials, the proportion of the present complexes in the total phosphorescent materials is preferably from 0.1 to 60% by mass, more preferably from 0.2 to 50% by mass, still more preferably from 0.3 to 40% by mass, especially preferably from 0.5 to 35% by mass.

<Host Material>

The host material is preferably a charge transport material. The host material may be made up of either only one kind of material or two or more kinds of materials. For example, the host material may contain an electron-transportable host material and a hole-transportable host material in the form of a mixture. Further, a material having neither charge transportability nor luminescent property may be included in the light emitting layer.

The term "host material" refers to a compound which mainly assumes the roles of a charge injector and a charge transporter in the light emitting layer, and besides, which in itself emits substantially no light. The expression of "emit substantially no light" in this specification means that the amount of light emitted from the compound emitting substantially no light is preferably at most 5%, more preferably at most 3%, still more preferably at most 1%, of the total amount of light emitted from the whole device.

The proportion of a host material contained in the light emitting layer is not particularly limited, but it is preferable that the host material is a main component (a component whose content is the highest) in the light emitting layer, and more specifically, the host material content is preferably from 50 mass % to 99.9 mass %, more preferably from 70 mass % to 99.8 mass %, still more preferably from 80 mass % to 99.7 mass %, especially preferably from 90 mass % to 99.5 mass %.

The glass transition temperature of the host material is preferably from 100° C. to 500° C., more preferably from 110° C. to 300° C., still more preferably from 120° C. to 250° C.

In the invention, the fluorescence wavelength of the host material present in a state of film in the light emitting layer is preferably in a range of 400 nm to 650 nm, more preferably in a range of 420 nm to 600 nm, still more preferably in a range of 440 nm to 550 nm.

Examples of a host material suitably used in the invention include the compounds disclosed in JP-A-2002-100476, paragraphs [0113] to [016], and the compounds disclosed in JP-A-2004-214179, paragraphs [0087] to [0098], but they should not be construed as being limited to these compounds.

Examples of a host material contained in the light emitting layer according to the invention include materials having carbazole skeletons, those having diarylamine skeletons, those having pyridine skeletons, those having pyrazine skeletons, those having triazine skeletons and those having arylsilane skeletons, and further include the materials recited in the following sections under Hole Injection Layer, Electron Injection Layer and Electron Transport Layer. Of such materials, the materials having tertiary amine skeletons, carbazole skeletons or indole skeletons are preferable to the others. In particular, the materials having carbazole skeletons are preferred.

-Hole Injection Layer, Hole Transport Layer-

A hole injection layer or a hole transport layer has a function of receiving holes from the anode or anode side and transporting them to the cathode side. The hole injection layer or the hole transport layer is preferably a layer containing a carbazole derivative, an azacarbazole derivative, an indole derivative, an azaindole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styryl amine compound, an aromatic dimethylidyne compound, a porphyrine compound, an organosilane derivative, carbon, or various metal complexes typified by an Ir complex having phenylazole or phenylazine as a ligand.

The hole injection layer or the hole transport layer of the organic EL device of the invention may contain an electron accepting dopant. As the electron accepting dopant to be introduced into the hole injection layer or the hole transport layer, any of inorganic compounds and organic compounds is usable insofar as it can accept electrons and oxidize an organic compound.

Specific examples of the inorganic compound include metal halides such as ferric chloride, aluminum chloride, gallium chloride, indium chloride, and antimony pentachloride, and metal oxides such as vanadium pentaoxide and molybdenum trioxide.

As the organic compound, compounds having, as a substituent, a nitro group, a halogen atom, a cyano group, or a trifluoromethyl group; quinone compounds, acid anhydride compounds, and fullerenes are preferred.

In addition, those described in JP-A-6-212153, JP-A-11-111463, JP-A-11-251067, JP-A-2000-196140, JP-A-2000-286054, JP-A-2000-315580, JP-A-2001-102175, JP-A-2001-160493, JP-A-2002-252085, JP-A-2002-56985, JP-A-2003-157981, JP-A-2003-217862, JP-A-2003-229278, JP-A-2004-342614, JP-A-2005-72012, JP-A-2005-166637, and JP-A-2005-209643 are preferred.

Of these, particularly preferred are hexacyanobutadiene, hexacyanobenzene, tetracyanoethylene, tetracyanoquinodimethane, tetrafluorotetracyanoquinodimethane, p-fluoranil, p-chloranil, p-bromanil, p-benzoquinone, 2,6-dichlorobenzoquinone, 2,5-dichlorobenzoquinone, 1,2,4,5-tetracyanobenzene, 1,4-dicyanotetrafluorobenzene, 2,3-dichloro-5,6-dicyanobenzoquinone, p-dinitrobenzene, m-dinitrobenzene, o-dinitrobenzene, 1,4-naphthoquinone, 2,3-dichloronaphthoquinone, 1,3-dinitronaphthalene, 1,5-dinitronaphthalene, 9,10-anthraquinone, 1,3,6,8-tetranitrocarbazole, 2,4,7-trinitro-9-fluorenone, 2,3,5,6-tetracyanopyridine, and fullerene C60. Of these, hexacyanobutadiene, hexacyanobenzene, tetracyanoethylene, tetracyanoquinodimethane, tetrafluorotetracyanoquinodimethane, p-fluoranil, p-chloranil, p-bromanil, 2,6-dichlorobenzoquinone, 2,5-dichlorobenzoquinone, 2,3-dichloronaphthoquinone, 1,2,4,5-tetracyanobenzene, 2,3-dichloro-5,6-dicyanobenzoquinone and 2,3,5,6-tetracyanopyridine are more preferred, with tetrafluorotetracyanoquinodimethane being especially preferred.

These electron-accepting dopants may be used either singly or in combination. The amount of the electron-accepting dopants differs, depends on the kind of the materials, but the amount is preferably from 0.01 to 50 mass %, more preferably from 0.05 to 20 mass %, especially preferably from 0.1 to 10 mass %, each relative to the materials of the hole transport layer.

The thickness of each of the hole injection layer and the hole transport layer is preferably 500 nm or less in order to reduce the driving voltage.

The thickness of the hole transport layer is preferably from 1 to 500 nm, more preferably from 5 nm to 200 nm, still more preferably from 10 nm to 100 nm. The thickness of the hole injection layer is preferably from 0.1 nm to 200 nm, more preferably from 0.5 to 100 nm, still more preferably from 1 to 100 nm.

The transport injection layer and the hole transport layer may each be a single layer composed of one or more of the above-described materials or a multilayer composed of a plurality of layers having the same composition or different compositions.

-Electron Injection Layer, Electron Transport Layer-

The electron injection layer and the electron transport layer are layers having a function of receiving electrons from the cathode or the cathode side and transporting them to the anode side.

Specifically, the electron injection layer and the electron transport layer are preferably layers containing a triazole derivative, an oxazole derivative, an oxadiazole derivative, an imidazole derivative, a fluorenone derivative, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, an aromatic cyclic tetracarboxylic anhydride such as naphthalene and perylene, various complexes typified by a complex of a 8-quinolinol derivative, metalphthalocyanines, and complexes having benzoxazole or benzothiazole as a ligand, and organic silane derivatives.

The electron injection layer or the electron transport layer of the organic EL device of the invention can contain an electron donating dopant. The electron donating dopant to be introduced into the electron injection layer or the electron transport layer may be any material insofar as it has an electron donating property and therefore capable of reducing an organic compound. Alkali metals such as Li, alkaline earth metals such as Mg, transition metals containing a rare earth metal, and reductive organic compounds are preferred. As the metal, those having a work function not greater than 4.2 eV are especially preferred. Specific examples of it include Li, Na, K, Be, Mg, Ca, Sr, Ba, Y, Cs, La, Sm, Gd, and Yb. The reductive organic compounds are, for example, nitrogen-containing compounds, sulfur-containing compounds, and phosphorus-containing compounds.

In addition, materials described in JP-A-6-212153, JP-A-2000-196140, JP-A-2003-68468, JP-A-2003-229278, and JP-A-2004-342614 can be used.

These electron donating dopant may be used either singly or in combination. The amount of the electron donating dopant varies, depending on the kind of the material, but it is preferably from 0.1 to 99 mass %, more preferably from 1.0 to 80 mass %, especially preferably from 2.0 to 70 mass % relative to the material of the electron transport layer.

The thickness of each of the electron injection layer and the electron transport layer is preferably 500 nm or less in order to reduce the driving voltage.

The thickness of the electron transport layer is preferably from 1 to 500 nm, more preferably from 5 nm to 200 nm, still more preferably 10 nm to 100 nm. The thickness of the electron injection layer is preferably from 0.1 to 200 nm, more preferably from 0.2 to 100 nm, still more preferably from 0.5 to 50 nm.

Each of the electron injection layer and the electron transport layer may be a single layer composed of one or more of the above-described materials or a multilayer composed of a plurality of layers having the same composition or having different compositions.

-Hole Blocking Layer-

The hole blocking layer is a layer having a function of preventing passage of holes, which have been transported to the light emitting layer from the anode side, to the cathode side. In the invention, the hole blocking layer can be formed as an organic layer adjacent to the light emitting layer on the cathode side.

Examples of organic compounds constituting the hole blocking layer include aluminum complexes such as Aluminum (III)bis(2-methyl-8-quinolinato)4-phenylphenolate (abbreviated to BAlq), triazole derivatives, and phenanthroline derivatives such as 2,9-Dimethyl-4,7-diphenyl-1,10-phenanthroline (abbreviated to BCP). The thickness of the hole blocking layer is preferably from 1 to 500 nm, more preferably from 5 to 200 nm, still more preferably from 10 to 100 nm.

The hole blocking layer may be a single layer composed of one or more of the above-described materials or a multilayer composed of a plurality of layers having the same composition or different compositions.

<Protective Layer>

In the invention, the whole organic EL device may be protected by a protective layer.

Any material may be incorporated in the protective layer insofar as it has a function of preventing intrusion of substances, which promote deterioration of the device such as water or oxygen, into the device.

Specific examples of the material include metals such as In, Sn, Pb, Au, Cu, Ag, Al, Ti and Ni; metal oxides such as MgO, SiO, $SiO_2$, $Al_2O_3$, GeO, NiO, CaO, BaO, $Fe_2O_3$, $Y_2O_3$, and $TiO_2$; metal nitrides such as $SiN_x$ and $SiN_xO_y$; metal fluorides such as $MgF_2$, LiF, $AlF_3$ and $CaF_2$; polyethylene, polypropylene, poly(methyl methacrylate), polyimide, polyurea, polytetrafluoroethylene, polychlorotrifluoroethylene, polydichlorodifluoroethylene, chlorotrifluoroethylene/dichlorodifluoroethylene copolymer, copolymers obtainable by copolymerizing a monomer mixture containing tetrafluoroethylene and at least one comonomer, fluorine-containing copolymers having, on the copolymer backbone thereof, a ring structure, water absorptive materials having a water absorption of 1% or greater, and moisture-proof materials having a water absorption of 0.1% or less.

A process for forming the protective layer is not particularly limited. Examples of the process applicable to the formation include a vacuum deposition process, a sputtering process, a reactive sputtering process, a MBE (molecular beam epitaxy) process, a cluster ion beam process, an ion plating process, a plasma polymerization process (high-frequency excited ion plating process), a plasma CVD process, a laser CVD process, a thermal CVD process, a gas source CVD process, a coating process, a printing process, and a transfer process.

<Sealing Container>

The entire device of the invention may be sealed using a sealing container.

A space between the sealing container and the device may be filled with a moisture absorbent or an inert liquid. The moisture absorbent is not particularly limited. Examples of it include barium oxide, sodium oxide, potassium oxide, calcium oxide, sodium sulfate, calcium sulfate, magnesium sulfate, phosphorus pentaoxide, calcium chloride, magnesium chloride, copper chloride, cesium fluoride, niobium fluoride, calcium bromide, vanadium bromide, a molecular sieve, zeolite, and magnesium oxide. The inert liquid is not particularly limited and examples of it include paraffins, liquid paraffins, fluorine-based solvents such as perfluoroalkanes, perfluoroamines and perfluoroethers, chlorine-based solvents, and silicone oils.

<Driving>

By applying a direct current (which may contain an alternating current component if necessary) voltage (usually from 2 to 15V) or a direct current between the anode and the cathode of the device of the invention, light emission can be obtained.

Examples of a method for driving the device of the invention include those described JP-A-2-148687, JP-A6-301355, JP-A-5-29080, JP-A-7-134558, JP-A-8-234685, and JP-A-8-241047, Japanese Patent No. 2784615, and U.S. Pat. Nos. 5,828,429 and 6,023,308.

<Charge Generation Layer>

The organic EL element of the invention can have a charge generation layer between two or more light emitting layers in order to improve luminous efficiency.

The charge generation layer has a function of generating charges (holes and electrons) when a voltage is applied and at the same time has a function of injecting the charges thus generated into a layer adjacent to the charge generation layer.

The material for forming the charge generation layer may be any material insofar as it has the-above mentioned functions. The charge generation layer may be made of a single compound or a plurality of compounds.

Specifically, the material may be either conductive or semiconductive such as a doped organic layer. It may also be an insulating material. Examples include materials described in JP-A-11-329748, JP-A-2003-272860 and JP-A-2004-39617.

More specifically, examples may include transparent conductive materials such as ITO and IZO (indium zinc oxide), fullerenes such as C60, conductive organic materials such as oligothiophenes, conductive organic materials such as metallophthalocyanines, metal-free phthalocyanines, metalloporphyrins and metal-free porphyrins, metal materials such as Ca, Ag, Al, Mg:Ag alloys, Al:Li alloys and Mg:Li alloys, hole conductive materials, and electron conductive materials, and mixtures thereof.

Examples of the hole conductive materials include materials obtained by doping a hole transporting organic material such as 2-TNATA or NPD with an electron attractive oxidizing agent such as F4-TCNQ, TCNQ or $FeCl_3$, P-type conductive polymers and P-type semiconductors. Examples of the electron conductive materials include materials obtained by doping an electron transporting organic material with a metal or metal compound having a work function less than 4.0 eV, N-type conductive polymers and N-type semiconductors. Examples of the N-type semiconductors include N-type Si, N-type CdS and N-type ZnS. Examples of the P-type semiconductors include P-type Si, P-type CdTe and P-type CuO.

Further, insulating materials such as $V_2O_5$ can be used for the charge generation layer.

The charge generation layer may be a single layer or a stack of a plurality of layers. Examples of the latter one include a layer having a structure in which a transparent conductive material, a conductive material such as a metal material, and the hole conductive material or the electron conductive material are stacked one after another and a layer having a structure in which the hole conductive material and the electron conductive material are stacked one after another.

It is usually preferred to select the film thickness or the material of the charge generation layer to give light transmittance of 50% or greater. The thickness is not particularly limited, but preferably from 0.5 to 200 nm, more preferably from 1 to 100 nm, still more preferably from 3 to 50 nm, especially preferably from 5 to 30 nm.

The formation process of the charge generation layer is not particularly limited, and the above-described formation process of the organic compound layer can be employed.

The charge generation layer is inserted between the two or more light-emitting layers. The charge generation layer may contain, on the anode side and the cathode side thereof, a material having a function of injecting charges into an adjacent layer. In order to improve the electron injection property to the adjacent layer on the anode side, an electron injecting compound such as BaO, SrO, $Li_2O$, LiCl, LiF, $MgF_2$, MgO or $CaF_2$ may be stacked on the anode side of the charge generation layer.

Alternatively, the material of the charge generation layer can be selected based on the descriptions of JP-A-2003-45676 and U.S. Pat. Nos. 6,337,492, 6,107,734, and 6,872,472.

The device of the invention can be suitably used for display devices, displays, backlights, electrophotography, light sources for illumination, light sources for recording, light sources for exposure, light sources for reading, signs, sign boards, interiors, and optical communications.

EXAMPLES

Example 1

<Synthesis of Exemplified Compound 1>

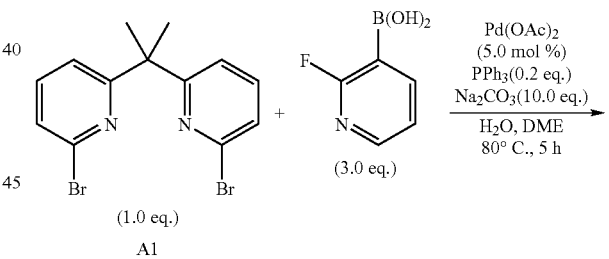

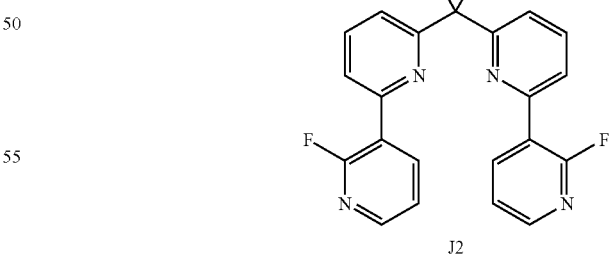

Synthesis of Compound J2

A mixture composed of Compound A1 (3.56 g, 10.0 mmol), 2-fluoropyridyl-3-boric acid (4.23 g, 30.0 mmol), palladium acetate (0.11 g, 0.5 mmol), triphenylphosphine (0.52 g, 2.0 mmol), sodium carbonate (10.6 g, 0.1 mol), 1.2-dimethoxyethane (100 mL) and water (100 mL) is stirred for 5 hours at 80° C. in a nitrogen atmosphere. After cooling to room temperature, the reaction mixture is filtered, followed by extraction with chloroform. The organic layers are combined, dried, and concentrated. The residue thus obtained is purified by column chromatography. Recrystallization from ethanol is then performed to yield 1.90 g of Compound J2 in the form of white crystals. The yield is 490%.

¹H-NMR (300 MHz, CDCl₃) δ: 1.93(s, 6H), 7.21(d, J=9.0Hz, 2H), 7.30(m, 2H), 7.69(t, J=9Hz, 2H), 7.78(d, J=6.0Hz, 2H), 8.23(m, 2H), 8.64(m, 2H).

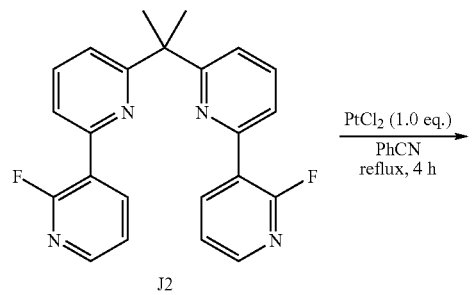

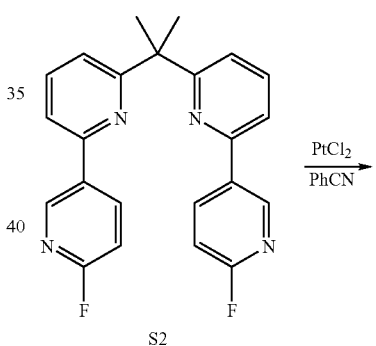

Exemplified Compound 1

Synthesis of Exemplified Compound 1

In benzonitrile (50 mL), platinum chloride (2.2 g, 5.0 mmol) and Compound J2 (2.2g, 5.0 mmol) are stirred for 4 hours under heating and refluxing conditions in a nitrogen atmosphere. The solvent is then distilled off from the reaction mixture. The residue thus obtained is purified by column chromatography and recrystallization to yield 2.6 g of Exemplified Compound 1 in the form of yellow powders. Yield: 76%.

¹H-NMR (300 MHz, CDCl₃) δ: 2.11 (s, 6H), 7.57 (d, J=8.4 Hz, 2H), 7.93 (t, J=8.1 Hz, 2H), 8.00 (dd, J=5.1, 3.0 Hz, 2H), 8.06 (dd, J=5.7, 5.1 Hz, 2H), 8.20 (d, J=8.4 Hz, 2H).

Example 2

<Synthesis of Exemplified Compound 2>

Synthesis of Compound S2

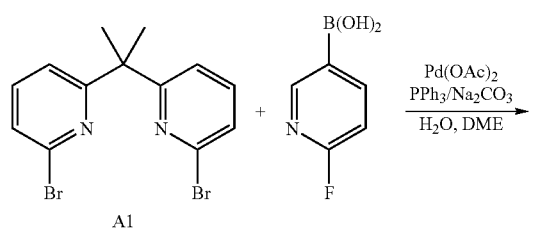

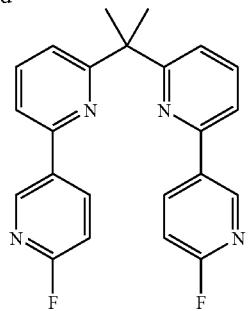

S2

A mixture composed of Compound A1 (0.83 g, 2.3 mmol), 6-fluoropyridyl-3-boric acid (1.0 g, 7.0 mmol), palladium acetate (26 mg, 0.12 mmol), triphenylphosphine (121 mg, 0.46 mmol), sodium carbonate (2.4 g, 23 mmol), 1,2-dimethoxyethane (25.0 mL) and water (25.0 mL) is stirred for 1.5 hours at 85° C. in a nitrogen atmosphere. After cooling to room temperature, the reaction mixture is filtered with cerite, followed by extraction with ethyl acetate. The organic layers are gathered up, dried, and then concentrated. The residue thus obtained is purified by column chromatography, thereby yielding 0.7 g of Compound S2 in the form of a white solid. The yield is 85%.

Synthesis of Exemplified Compound 2

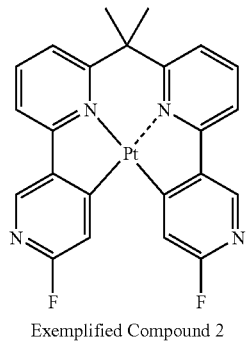

Exemplified Compound 2

In a nitrogen atmosphere, platinum chloride (137 mg, 0.52 mmol) and Compound S2 (200 mg, 0.52 mmol) are stirred into benzonitrile (5 mL) for 6.5 hours under heating and refluxing conditions. The reaction mixture is cooled to room temperature, and a solid precipitated out by addition of methanol is filtered off, and washed with methanol. Thus, Exemplified Compound 2 is obtained in the form of a yellow solid.

Example 3

Synthesis of Exemplified Compound 3

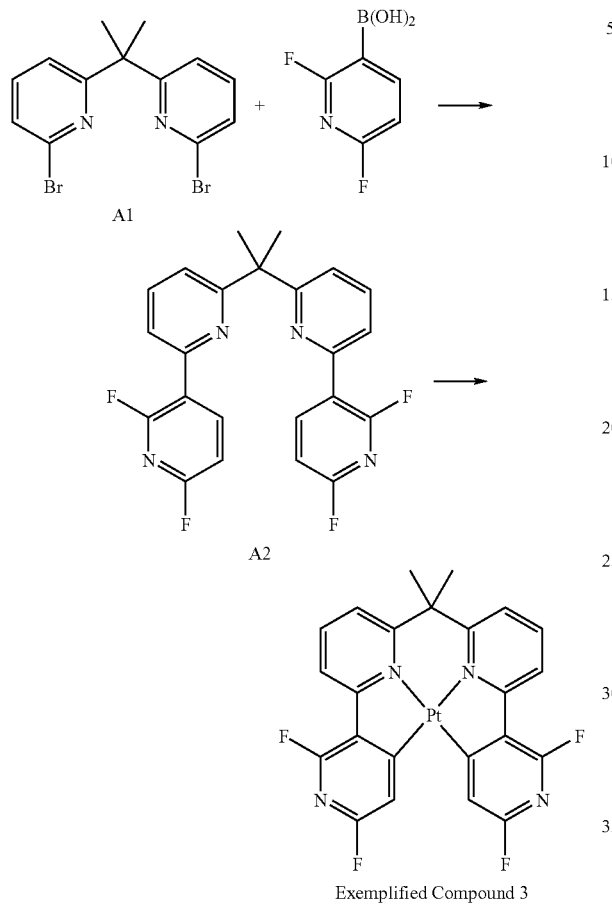

Exemplified Compound 3

Synthesis of Compound A2

In a nitrogen atmosphere, a three-necked flask is charged with Compound A1 (2.0 g, 5.62 mmol), 2,6-difluoropyridyl-3-boric acid (2.14 g, 11.24 mmol), palladium acetate (63 mg, 0.281 mmol), triphenylphosphine (294 mg, 1.12 mmol), sodium carbonate (5.96 g, 56.2 mmol), 1,2-dimethoxyethane (40 ml) and water (40 ml). The resulting mixture is heated under reflux for 6 hours and 30 minutes while stirring. After cooling to room temperature, the reaction mixture is extracted with ethyl acetate. The organic layer thus obtained is dried over sodium sulfate and filtered, followed by concentration. The residue obtained is purified by silica gel column chromatography (chloroform) to yield 1.81 g (yield: 76%) of Compound A2 in the form of white crystals.

$^1$H-NMR (CD$_2$Cl$_2$, 300 MHz,) δ: 1.95 (s, 6H), 7.00 (ddd, J=0.9, 3.0, 8.1 Hz, 2H), 7.30 (dd, J=2.4, 6.6 Hz, 2H), 7.74-7.80 (m, 4H), 8.72 (dt, J=8.1, 9.6 Hz, 2H)

Synthesis of Exemplified Compound 3

In a nitrogen atmosphere, a 100 mL eggplant flask is charged with Compound A2 (1.5 g, 3.53 mmol), platinum chloride (0.94 g, 3.53 mmol), and benzonitrile (50 mL). The resulting mixture is stirred at 180° C. for 6 hours. After cooling to room temperature, 150 mL of methanol is added to the reaction mixture. A solid thus precipitated is collected by filtration and dried under reduced pressure to yield 1.75 g (yield: 80%) of Exemplified Compound 3 in the form of yellow crystals. It has a λmax of 461 nm (dichloromethane solution).

$^1$H-NMR (CD$_2$Cl$_2$) 300 MHz, δ: 1.94 (s, 6H), 7.34 (tt, J=1.8, J(Pt—H)=56.4 Hz, 2H), 7.48 (dd, J=0.9, 7.8 Hz, 2H), 7.84 (t, J=8.1 Hz, 2H), 7.96 (d, J=8.4 Hz)

Example 4

<Synthesis of Exemplified Compound 25>

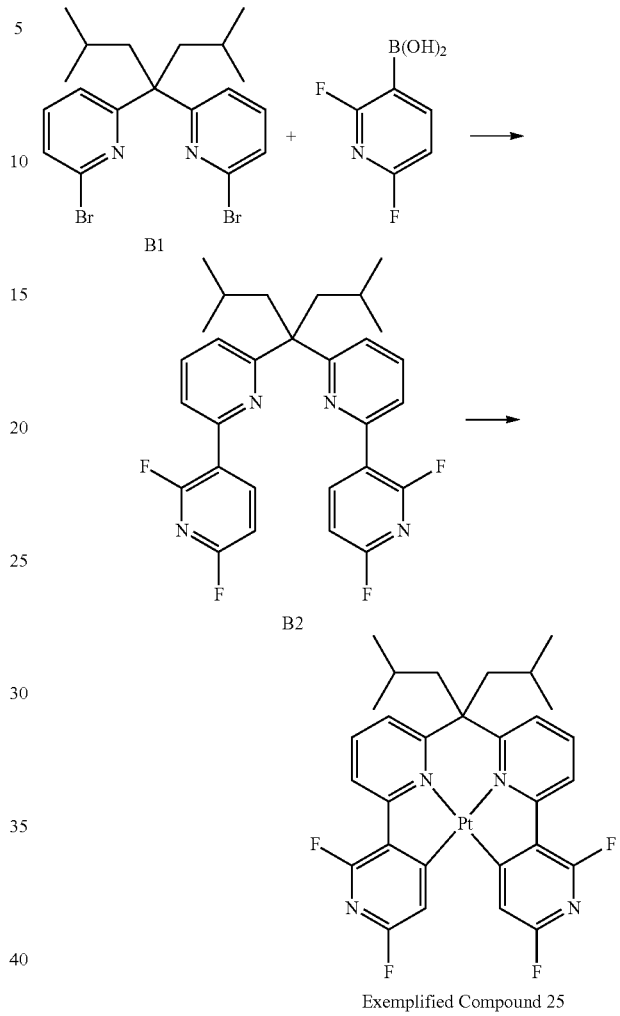

Exemplified Compound 25

Synthesis of Compound B2

A mixture composed of Compound B1 (2.2 g, 5.0 mmol), 2,6-difluoropyridyl-3-boric acid (2.4 g, 15.0 mmol), palladium acetate (56.1 mg, 0.25 mmol), triphenylphosphine (262.0 mg, 1.0 mmol), sodium carbonate (5.3 g, 50.0 mmol), 1,2-dimethoxyethane (50 mL) and water (50 mL) is stirred for 5 hours at 80° C. in a nitrogen atmosphere. After cooling to room temperature, the reaction mixture is filtered, followed by extraction with chloroform. The organic layers are combined, dried, and concentrated. The residue thus obtained is purified by column chromatography to yield 2.61 g of Compound B2 in the form of an yellow oil. Its yield is stoichiometric.

$^1$H-NMR (300 MHz, CDCl$_3$) δ: 0.61 (d, J=6.6 Hz, 12H), 1.63 (quint, J=6.0 Hz, 2H), 2.45 (d, J=5.4 Hz, 4H), 6.96 (d, J=9.0 Hz, 2H), 7.78 (dd, J=7.5, 0.3 Hz, 2H), 7.64 (t, J=7.8 Hz, 2H), 7.69 (t, J=7.5 Hz, 2H), 8.69 (dd, J=8.7, 8.4 Hz, 2H)

Synthesis of Exemplified Compound 25

Platinum chloride (2.2 g, 5.0 mmol) and Compound B2 (2.2 g, 5.0 mmol) are stirred for 4 hours in benzonitrile (50 mL) under heating and refluxing conditions in a nitrogen atmosphere. The solvent is distilled off from the reaction mixture. The residue thus obtained is purified by column chromatography and recrystallization to yield 2.6 g of Exemplified Compound 25 in the form of yellow powders. Yield: 76%

¹H-NMR (300 MHz, CDCl₃) δ: 0.51 (d, J=6.6 Hz, 12H), 1.17 (quint, J=6.3 Hz, 2H), 2.44 (d, J=6.4 Hz, 4H), 7.58 (s, 2H), 7.78 (d, J=8.7 Hz, 2H), 8.06 (t, J=8.1 Hz, 2H), 8.22 (d, J=8.1 Hz, 2H).

Example 5

<Synthesis of Exemplified Compound 26>
Synthesis of Compound K2

A mixture composed of Compound K1 (2.3 g, 6.0 mmol), 2,6-difluoropyridyl-3-boric acid (2.86 g, 18.0 mmol), palladium acetate (0.07 g, 0.3 mmol), triphenylphosphine (0.32 g, 1.2 mmol), sodium carbonate (6.38 g, 60.0 mol), 1,2-dimethoxyethane (60 mL), and water (60 mL) is stirred for 5 hours at 80° C. in a nitrogen atmosphere. After cooling to room temperatures the reaction mixture is filtered, followed by extraction with chloroform. The organic layers are combined, dried, and concentrated. The residue thus obtained is purified by column chromatography to yield 2.10 g of Compound K2 in the form of white crystals. The yield is 77%.

¹H-NMR (300 MHz, CDCl₃) δ: 1.78 (m, 4H), 2.67 (m, 2H), 6.99 (d, J=9.0 Hz, 2H), 7.24 (d, J=6.0 Hz, 2H), 7.66 (t, J=6.0 Hz, 2H), 7.69 (d, J=6.0 Hz, 2H), 6.78 (dd, J=9.8, 9.8, 2H).

Synthesis of Exemplified Compound 26

Platinum chloride (1.90 g, 4.2 mmol, 1.0 equivalent) and Compound K2 (1.12 g, 4.2 mmol, 1.0 equivalent) are stirred for 6 hours in benzonitrile (80 mL) under heating and refluxing conditions in a nitrogen atmosphere. The solvent is distilled off from the reaction mixture. The residue is purified by recrystallization to yield 2.05 g of Exemplified Compound 26 in the form of yellow crystals. Yield: 75%.

¹H-NMR (300 MHz, CDCl₃) δ: 1.77 (m, 4H), 2.76 (m, 4H), 7.49 (m, 4H), 7.92 (t, J=8.7 Hz, 2H), 8.08 (d, J=9.5 Hz, 2H)

Example 6

<Synthesis of Exemplified Compound 27>
Synthesis of Compound M2

A mixture composed of Compound M1 (3.4 g, 8.6 mmol), 2,6-difluoropyridyl-3-boric acid (4.2 g, 26.4 mmol), palladium acetate (96.2 mg, 0.43 mmol), triphenylphosphine (445.5 mg, 1.7 mmol), sodium carbonate (9.2 g, 86 mol, 5.0 equivalents), 1,2-dimethoxyethane (80.0 mL) and water (80.0 mL) is stirred for 1.5 hours at 80° C. in a nitrogen atmosphere. After cooling to room temperature, the reaction mixture is filtered, followed by extraction with chloroform. The organic layers are combined, dried, and concentrated. The residue thus obtained is purified by column chromatography to yield 3.4 g (yield: 84%) of Compound M2 in the form of a white solid.

$^1$H-NMR (300 MHz, CDCl$_3$) δ: 1.61-1.52 (m, 6H), 2.62-2.58 (m, 4H), 6.97 (dd, J=8.1, 2.7 Hz, 2H), 7.30-7.26 (m, 2H), 7.69-7.67 (m, 4H), 8.76 (q, J=9.3 Hz, 2H).

Synthesis of Exemplified Compound 27

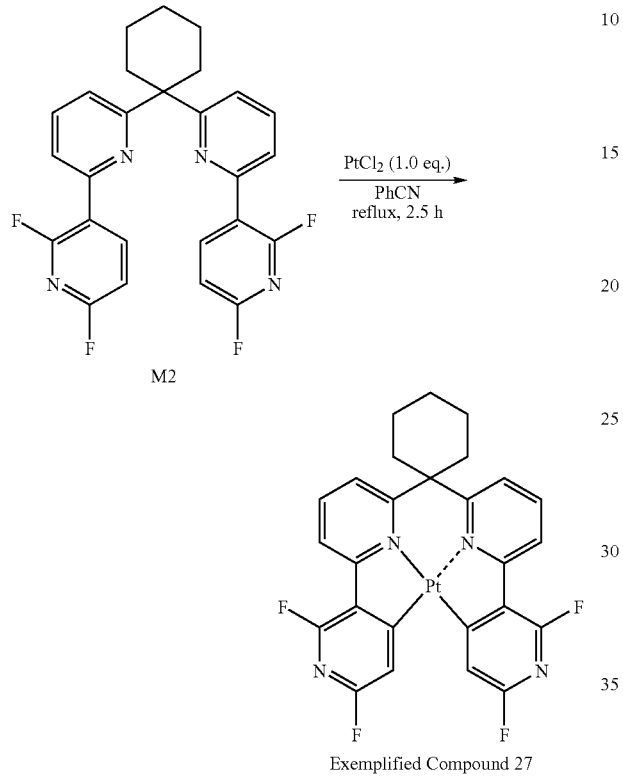

Exemplified Compound 27

Platinum chloride (2.66 g, 10.0 mmol) and Compound M2 (3.4 g, 7.3 mmol) are stirred in benzonitrile (70 mL) for 2.5 hours under heating and reflux conditions in a nitrogen atmosphere. The reaction mixture is allowed to cool to room temperature. A solid thus precipitated is filtered and washed with methanol to yield 3.2 g of Exemplified Compound 27 in the form of yellow powders. Yield: 75%.

$^1$H-NMR (300 MHz, CDCl$_3$) δ: 1.22 (br, 2H), 1.47 (br, 2H), 1.92 (br, 2H), 2.61 (br, 2H), 2.99 (br, 2H), 7.48 (m, J(Pt—H)=60.0 Hz, 2H), 7.56-7.53 (m, 2H), 7.95 (t, J=9.0 Hz, 2H), 8.08 (d, J=9.0 Hz, 2H).

Example 7

<Synthesis of Exemplified Compound 31>

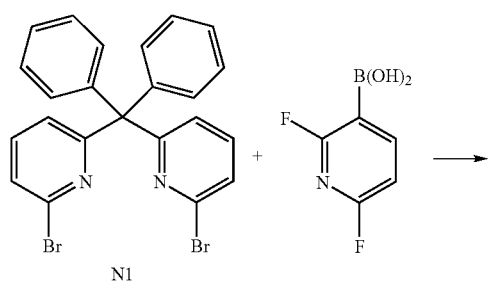

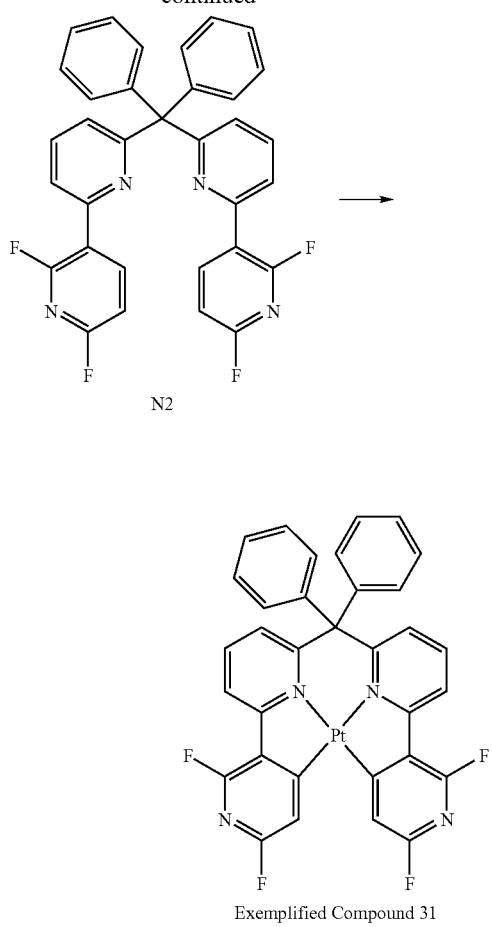

Exemplified Compound 31

Synthesis of Compound N2

In a nitrogen atmosphere, a three-necked flask is charged with Compound N1 (3.0 g, 6.24 mmol), 2,6-difluoropyridyl-3-boric acid (2.38 g, 15 mmol), palladium acetate (70 mg, 0.31 mmol), triphenylphosphine (327 mg, 1.24 mmol), sodium carbonate (6.61 g, 62.4 mmol), 1,2-dimethoxyethane (50 ml) and water (50 ml). The resulting mixture is heated under reflux for 6 hours while stirring. After cooling to room temperature, the reaction mixture is extracted with ethyl acetate. The organic layer thus obtained is dried over sodium sulfate and filtered, followed by concentration. The residue obtained is purified by silica gel column chromatography (chloroform) to yield Compound N2 in the form of a beige solid.

Synthesis of Exemplified Compound 31

In a nitrogen atmosphere, a 100-mL egg-plant type flask is charged with Compound N2 (1 g, 1.82 mmol), platinum chloride (484 mg, 1.82 mmol) and benzonitrile (30 mL), and the resulting mixture is stirred at 180° C. for 6 hours. After cooling to room temperature, the reaction mixture is admixed with 50 mL of ethanol to precipitate a solid. The solid thus precipitated is filtered off, and dried under reduced pressure, thereby yielding 600 mg (yield: 44%) of Exemplified Compound 31 in the form of yellow crystals.

$^1$H-NMR (CD$_2$Cl$_2$) 300 MHz δ: 6.63-6.70 (m, 4H), 7.08-7.19 (m, 2H), 7.32-7.42 (m, 8H), 7.91 (t, J=8.1 Hz, 2H), 8.25 (d, J=8.4 Hz, 2H).

Example 8

<Synthesis of Exemplified Compound 37>

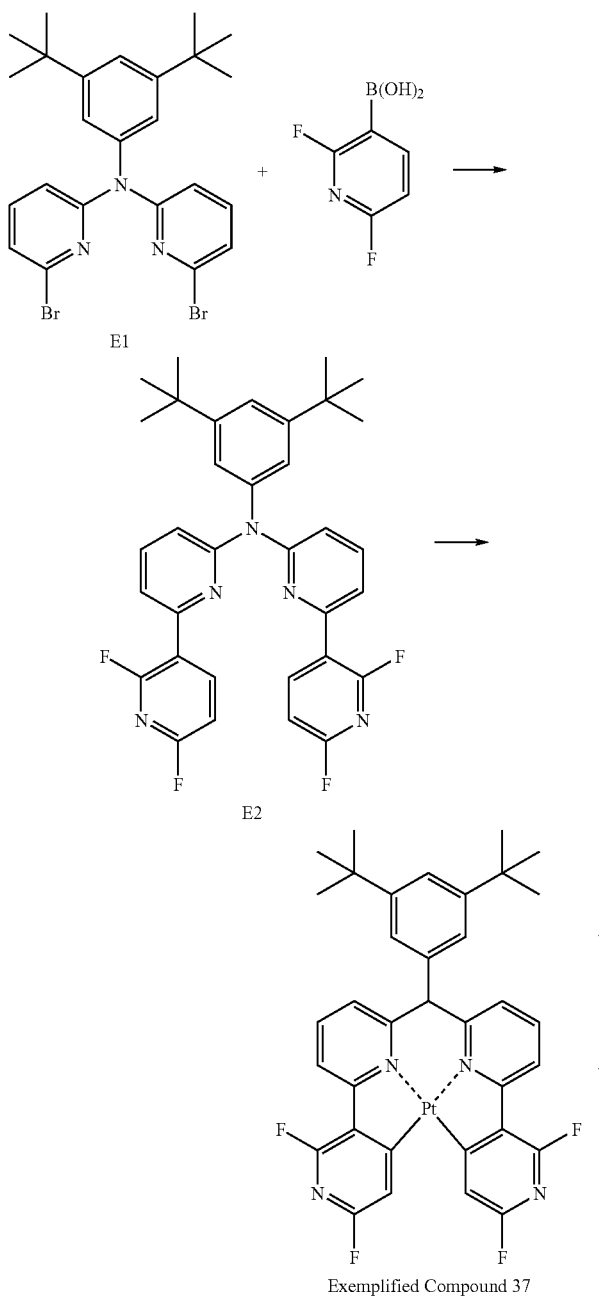

Exemplified Compound 37

Synthesis of Compound E2

In a nitrogen atmosphere, a mixture of Compound E1 (700 mg, 1.35 mmol), 2,6-difluoropyridyl-3-boric acid (2.1 g, 13.5 mmol), palladium acetate (30.3 mg, 0.14 mmol), triphenylphosphine (142.0 mg, 0.54 mmol), potassium carbonate (1.9 g, 13.5 mmol), 1,2-dimethoxyethane (7.0 ml) and water (7.0 ml) are stirred at 80° C. for 8.5 hours. After cooling to room temperature, the reaction mixture is filtered, and then extracted with ethyl acetate. The organic layers thus obtained are gathered up and dried, followed by concentration. The residue obtained is purified by column chromatography to yield 501.1 mg (yield: 63%) of Compound E2 in the form of yellow oily matter.

$^1$H-NMR (300 MHz, CDCl$_3$) δ: 1.30 (s, 18H), 6.78 (dd, J=8.1, 3.0 Hz, 2H), 7.12-7.07 (m, 4H), 7.38 (t, J=1.8 Hz, 1H), 7.56 (dd, J=7.5, 1.8 Hz, 2H), 7.67 (t, J=7.8 Hz, 2H), 8.35 (t, J=8.1 Hz, 1H), 8.39 (t, J=8.1 Hz, 1H).

Synthesis of Exemplified Compound 37

In a nitrogen atmosphere, platinum chloride (300 mg, 0.86 mmol) and Compound E2 (501.1 mg, 0.86 mmol) are stirred into benzonitrile (10 mL) for 7 hours under heating and refluxing conditions. The solvent is distilled away from the reaction mixture, and the resulting residue is filtered off, and washed with methanol, thereby yielding 490 mg of the platinum complex in the form of a yellow powder. The yield is 73%.

$^1$H-NMR (300 MHz, CD$_2$Cl$_2$) δ: 1.31 (s, 18H), 6.58 (d, J=8.7 Hz, 2H), 7.19 (d, J=1.8 Hz, 2H), 7.43 (tt, J=1.5 Hz, J(Pt—H)=55.8 Hz, 2H), 7.52 (m, 1H), 7.76 (t, J=8.7 Hz, 2H), 7.88 (d, J=8.1 Hz, 2H).

Example 9

<Synthesis of Exemplified Compound 43>

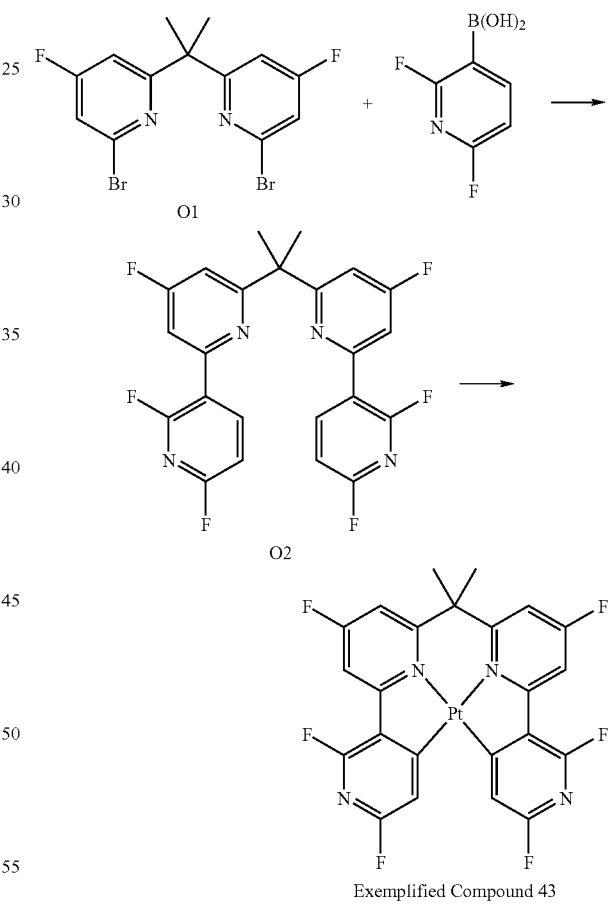

Exemplified Compound 43

Synthesis of Compound O2

In a nitrogen atmosphere, a three-necked flask is charged with Compound O1 (1.25 g, 3.2 mmol), 2,6-difluoropyridyl-3-boric acid (1.22 g, 7.68 mmol), palladium acetate (71.7 mg, 0.32 mmol), triphenylphosphine (340 mg, 1.28 mmol), potassium carbonate (5.91 g, 42.2 mmol), tetrahydrofuran (30 ml) and water (30 ml). The resulting mixture is heated under reflux for 6 hours while stirring. After cooling to room temperature, the reaction mixture is extracted with ethyl acetate. The organic layer thus obtained is dried over sodium sulfate and filtered, followed by concentration. The residue obtained is purified by silica gel column chromatography to yield 0.94 g of Compound O2 in the form of a white solid.

Synthesis of Exemplified Compound 43

In a nitrogen atmosphere, a 100-mL egg-plant type flask is charged with Compound O2 (450 mg, 0.98 mmol), platinum chloride (260 mg, 0.98 mmol) and benzonitrile (10 mL), and the resulting mixture is stirred at 180° C. for 2 hours. After cooling to room temperature, the reaction mixture is admixed with 50 mL of ethanol to precipitate a solid. The solid thus precipitated is filtered off, and dried under reduced pressure, thereby yielding 270 mg of Exemplified Compound 43 in the form of yellow crystals.

$^1$H-NMR (CD$_2$Cl$_2$) 300 MHz δ: 2.08 (s, 6H), 7.41 (dd, J=2.4, 9.3 Hz, 2H), 7.51 (s, J(H–Pt)=57.6 Hz, 2H), 7.89 (dt, J=1.8, 9.0 Hz, 2H).

Example 10

<Synthesis of Exemplified Compound 46>

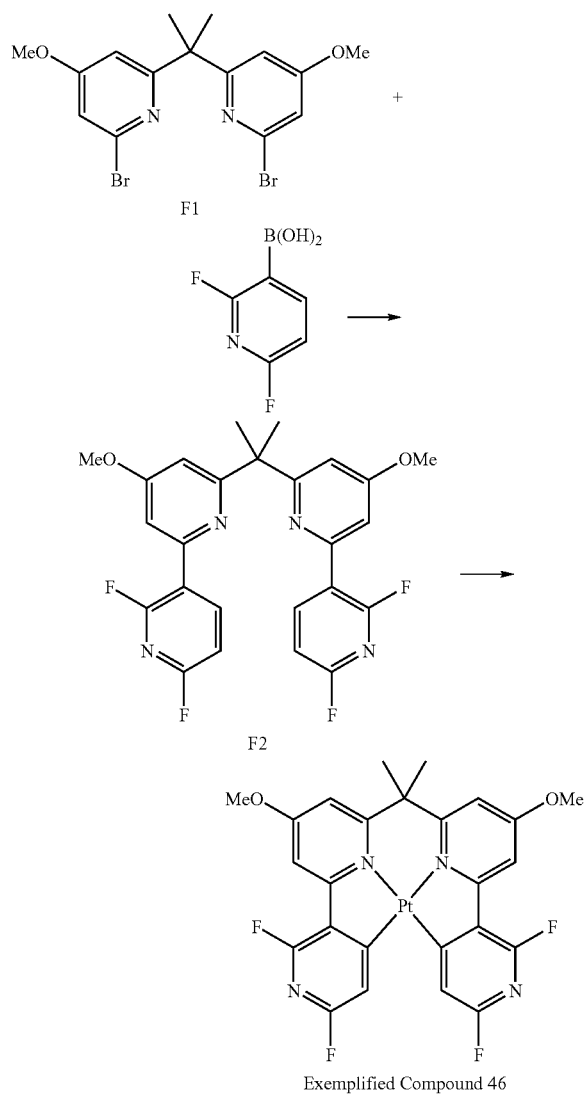

Synthesis of Compound F2

In a nitrogen atmosphere, a three-necked flask is charged with Compound F1 (0.8 g, 2.25 mmol), 2,6-difluoropyridyl-3-boric acid (858 mg, 5.4 mmol), palladium acetate (25 mg, 0.11 mmol), triphenylphosphine (118 mg, 0.45 mmol), sodium carbonate (2.38 g, 22.5 mmol), 1,2-dimethoxyethane (20 ml) and water (20 ml). The resulting mixture is heated under reflux for 6 hours while stirring. After cooling to room temperature, the reaction mixture is extracted with ethyl acetate. The organic layer thus obtained is dried over sodium sulfate and filtered, followed by concentration. The residue obtained is purified by silica gel column chromatography (chloroform) to yield 0.86 g (yield: 79%) of Compound F2 in the form of a beige solid, $^1$H-NMR (CDCl$_3$) 300 MHz δ: 1.86 (s, 6H), 3.84 (s, 6H), 6.73 (d, J=2.1 Hz, 2H), 6.94 (ddd, J=0.6, 3.0, 8.4 Hz, 2H), 7.26-7.29 (m, 2H), 8.74 (dt, J=8.1, 12.8 Hz, 2H).

Synthesis of Exemplified Compound 46

In a nitrogen atmosphere, a 100-mL egg-plant type flask is charged with Compound F2 (700 mg, 1.44 mmol), platinum chloride (383 mg, 1.44 mmol) and benzonitrile (35 mL), and the resulting mixture is stirred at 180° C. for 2 hours. After cooling to room temperature, the reaction mixture is admixed with 50 mL of methanol to precipitate a solid. The solid thus precipitated is filtered off, and dried under reduced pressure, thereby yielding 457 mg (yield: 48%) of Exemplified Compound 46 in the form of yellow crystals.

$^1$H-NMR (CD$_2$Cl$_2$, 300 MHz) δ: 2.03 (s, 6H), 4.05 (s, 6H), 7.14 (d, J=2.4 Hz, 2H), 7.50 (brs, J(H–Pt)=57.0 Hz, 2H), 7.62 (t, J=2.1 Hz, 2H).

Example 11

<Synthesis of Exemplified Compound 47>
Synthesis of Compound P2

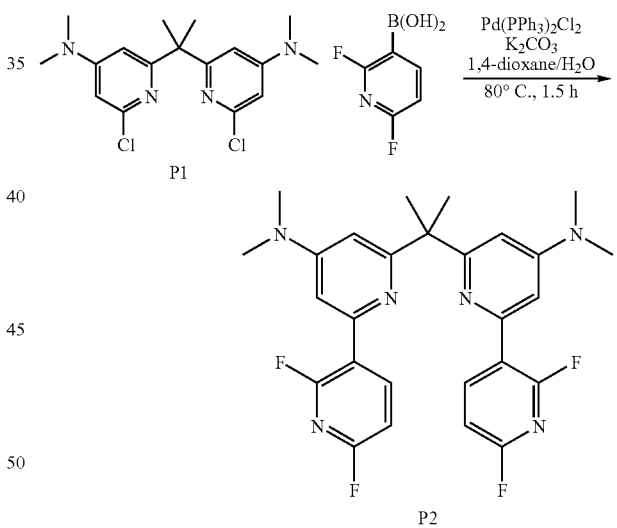

A mixture of Compound P1 (1.0 g, 2.9 mmol), 2,6-difluoropyridyl-3-boric acid (1.4 g, 8.5 mmol), dichlorobis(triphenylphosphine)palladium(II) (200 mg, 0.94 mmol), potassium carbonate (2.4 g, 6.0 mmol), water (102 mg, 5.7 mmol) and dioxane (30.0 mL) is heated under reflux for 4.5 hours in a nitrogen atmosphere. The reaction mixture is cooled to room temperature, filtered, admixed with water, and then extracted with ethyl acetate. The organic layers are gathered up, dried, and further concentrated. The resulting residue is purified by column chromatography to yield 730 mg (yield: 50%) of Compound P2 in the form of a white solid.

$^1$H-NMR (300 MHz, CDCl$_3$) δ: 186 (s, 6H), 3.01 (s, 12H), 6.43 (s, 2H), 6.93 (dd, J=3.0, 8.4 Hz, 2H), 7.02 (s, 2H), 8.79 (dt, J=8.1, 9.6 Hz, 2H).

Synthesis of Exemplified Compound 47

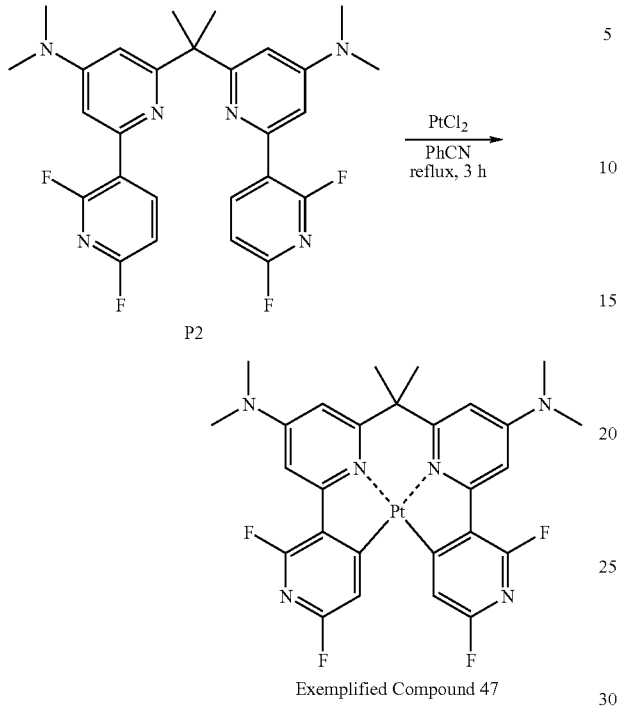

Exemplified Compound 47

In a nitrogen atmosphere, platinum chloride (193 mg, 0.72 mmol) and Compound P2 (370 mg, 0.72 mmol) are stirred into benzonitrile (7.0 mL) for 3 hours under heating and refluxing conditions. The reaction mixture is cooled to room temperature, and a solid precipitated out by addition of methanol is filtered off, and washed with methanol. Thus, 370 mg of Exemplified Compound 47 is obtained in the form of a light yellow powder. The yield is 73%.

$^1$H-NMR (300 MHz, $CD_2Cl_2$) δ: 2.02 (s, 6H), 3.20 (s, 12H), 6.75 (d, J=2.4 Hz, 2H), 7.30 (t, J=2.4 Hz, 2H), 7.48 (t, J(H—H)=2.1 Hz, J(Pt—H)=54.6 Hz, 2H).

Example 12

<Synthesis of Exemplified Compound 54>

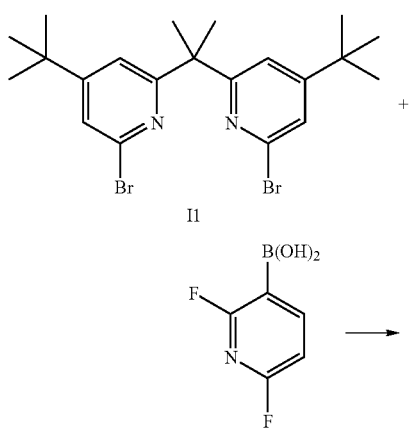

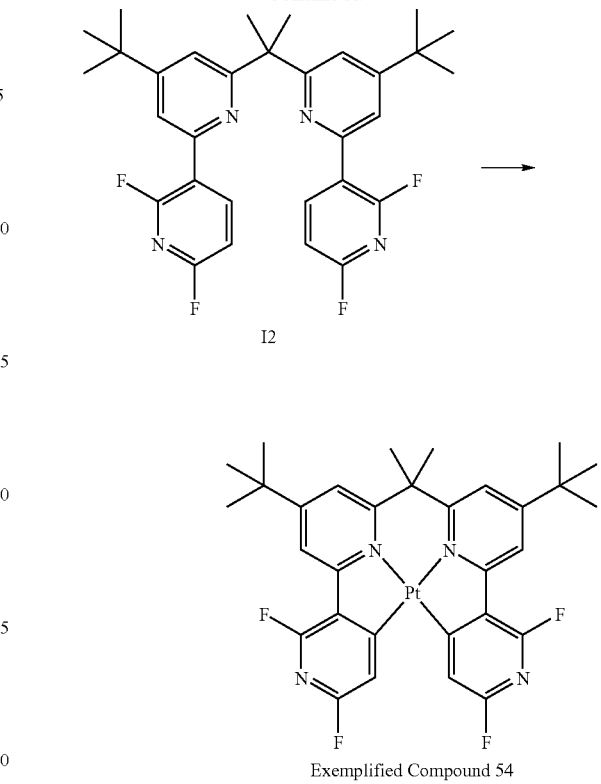

Exemplified Compound 54

Synthesis of Compound 12

In a nitrogen atmosphere, a three-necked flask is charged with Compound I1 (0.95 g, 2.03 mmol), 2,6-difluoropyridyl-3-boric acid (1.28 g, 8.12 mmol), palladium acetate (23 mg, 0.11 mmol), triphenylphosphine (106 mg, 0.41 mmol), potassium carbonate (2.80 g, 20.3 mmol), tetrahydrofuran (20 ml) and water (10 ml). The resulting mixture is heated under reflux for 5 hours while stirring. After cooling to room temperature, the reaction mixture is extracted with ethyl acetate. The organic layer thus obtained is dried over sodium sulfate and filtered, followed by concentration. The residue obtained is purified by silica gel column chromatography (hexane/ethyl acetate=20/1) to yield 1.04 g (yield: 95%) of Compound I2 in the form of a white solid.

$^1$H-NMR ($CD_2Cl_2$, 300 MHz) δ: 1.21 (s, 9H), 1.81 (s, 6H), 7.00 (ddd, J=0.6, 3.0, 8.4 Hz, 2H), 7.15 (d, J=1.8 Hz, 2H), 7.63 (t, J=1.8 Hz, 2H), 8.59 (dt, J=8.1, 9.6 Hz, 2H).

Synthesis of Exemplified Compound 54

In a nitrogen atmosphere, a 100-mL eggplant type flask is charged with Compound I2 (830 mg, 1.55 mol), platinum chloride (411 mg, 1.55 mmol), and benzonitrile (40 mL). The resulting mixture is stirred at 180° C. for 2 hours. After cooling to room temperature, 50 mL of methanol is added to the reaction mixture. A solid thus precipitated is filtered and dried under reduced pressure to yield 736 mg (yield: 65%) of Exemplified Compound 54 in the form of yellow crystals.

$^1$H-NMR ($CD_2Cl_2$, 300 MHz) 6; 1.44 (s, 9H), 2.12 (s, 6H), 7.51 (tt, J=1.5 Hz, J(Pt—H)=56.4 Hz, 2H), 7.63 (d, J=1.5 Hz, 2H), 8.14 (t, J=1.5 Hz, 2H).

Example 13

<Synthesis of Exemplified Compound 55>
Synthesis of Compound G2

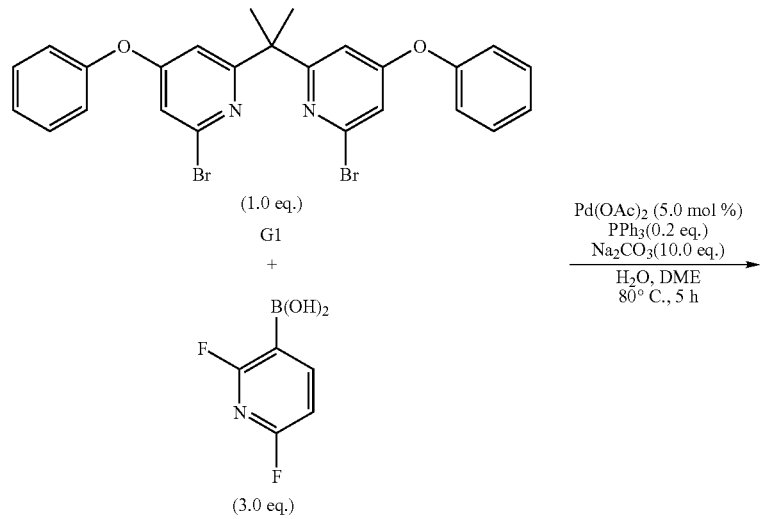

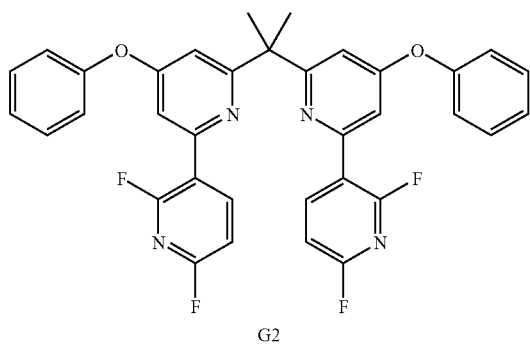

A mixture composed of Compound G1 (2.16 g, 4.0 mmol), 2,6-difluoropyridyl-3-boric acid (1.90 g, 12.0 mmol), palladium acetate (45 mg, 0.2 mmol), triphenylphosphine (0.21 g, 0.8 mmol), sodium carbonate (4.24 g, 40.0 mmol), 1,2-dimethoxyethane (40 mL), and water (40 mL) is stirred at 80° C. for 5 hours in a nitrogen atmosphere. After cooling to room temperature, the reaction mixture is filtered, followed by extraction with chloroform. The organic layers are combined, dried and concentrated. The residue thus obtained is purified by column chromatography to yield 2.26 g of Compound 62 in the form of white crystals.

Yield: 93%.

$^1$H-NMR (300 MHz, CDCl$_3$) δ: 1.85 (s, 6H), 6.85 (s, 2H), 6.92 (dd, J=5.1, 3.0 Hz, 2H), 7.06 (d, J=6.3 Hz, 4H), 7.23 (t, J=7.2 Hz, 2H), 7.34-7.44 (m, 6H), 8.66 (dt, J=9.3, 7.8 Hz, 2H).

Synthesis of Exemplified Compound 55

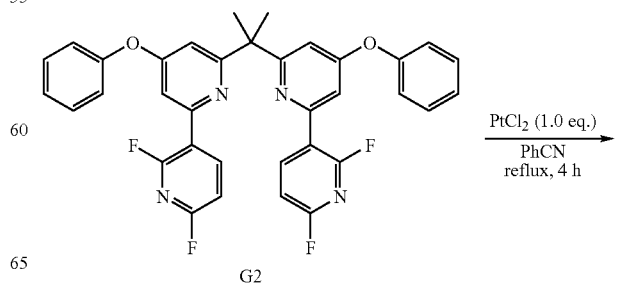

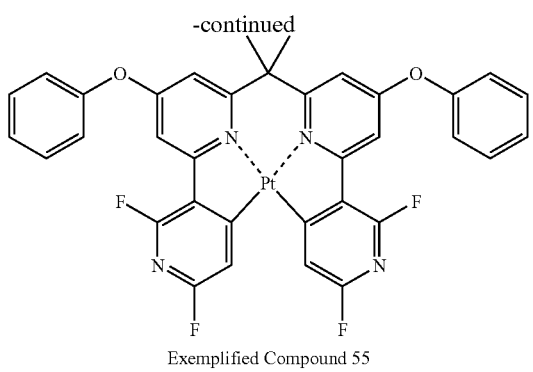

Exemplified Compound 55

Platinum chloride (0.79 g, 3.0 mmol) and Compound G2 (1.82 g, 3.0 mmol, 1.0 equivalent) are stirred for 4 hours in benzonitrile (30 mL) under heating and refluxing conditions in a nitrogen atmosphere. The solvent is distilled off from the reaction mixture. The residue thus obtained is purified by column chromatography and recrystallization to yield 1.8 g of Exemplified Compound 55 in the form of yellow powders. Yield: 76%.

$^1$H-NMR (300 MHz, CDCl$_3$) δ: 1.94 (s, 6H), 7.11 (t, J=4.8 Hz, 4H), 7.16 (s, 2H), 7.33 (t, J=7.5 Hz, 2H), 7.45 (d, J=7.2 Hz, 4H), 7.50 (s, 2H), 7.53 (t, J=2.1 Hz, 2H).

Example 14

<Synthesis of Exemplified Compound 86>
Synthesis of Compound H2

A mixture composed of Compound H1 (3.0 g, 5.0 mmol), 2,6-difluoropyridyl-3-boric acid (2.4 g, 15.0 mmol), palladium acetate (56.1 mg, 0.25 mmol), triphenylphosphine (262.0 mg, 140 mmol), sodium carbonate (5.3 g, 50.0 mmol), 1,2-dimethoxyethane (50 mL), and water (50 mL) is stirred at 80° C. for 5 hours in a nitrogen atmosphere. After cooling to room temperatures the reaction mixture is filtered, followed by extraction with chloroform. The organic layers are combined, dried and concentrated. The residue thus obtained is purified by column chromatography to yield 3.3 g of Compound H2 in the form of white crystals. Yield-98%.

$^1$H-NMR (300 MHz, CDCl$_3$) δ: 1.78 (s, 6H), 2.02 (s, 12H), 6.53 (s, 2H), 6.90 (dd, J=5.4, 3.0 Hz, 2H), 7.04 (s, 4H), 7.09 (s, 2H), 8.63 (dt, J9.6, 8.1 Hz, 2H).

Synthesis of Exemplified Compound 86

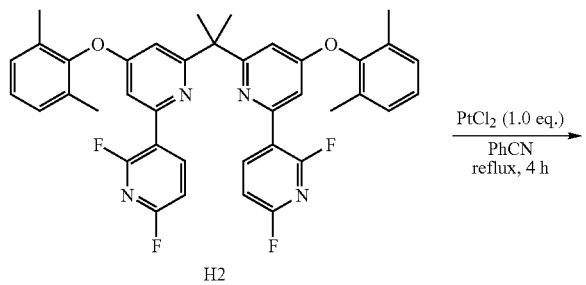

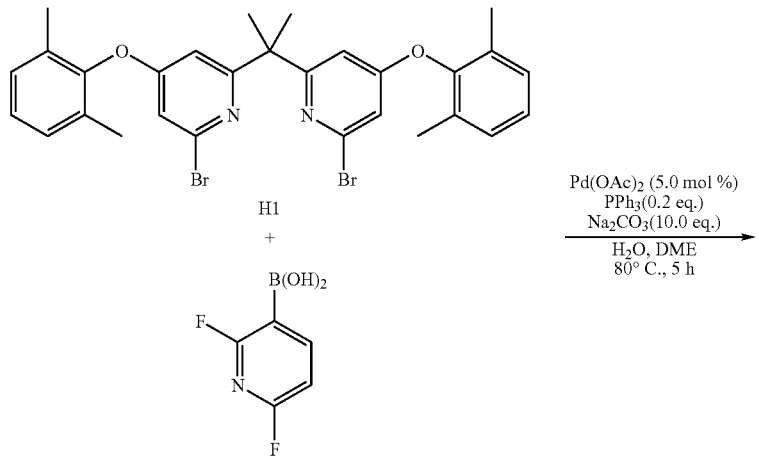

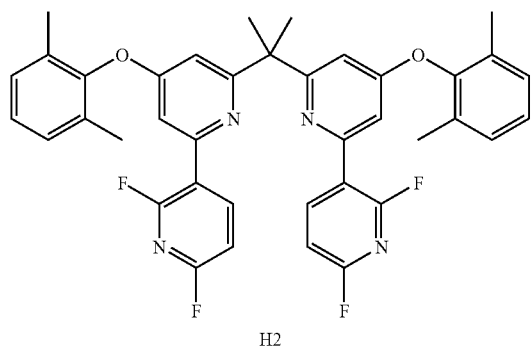

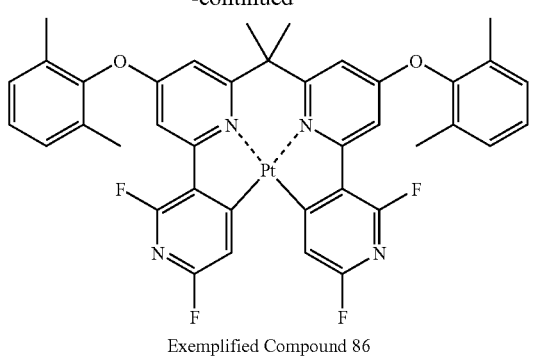

Exemplified Compound 86

Platinum chloride (1.12 g, 4.2 mmol) and Compound H2 (2.80 g, 4.2 mmol, 1.0 equivalent) are stirred for 4 hours in benzonitrile (42 mL) under heating and refluxing conditions in a nitrogen atmosphere. The solvent is distilled off from the reaction mixture. The residue thus obtained is purified by column chromatography and recrystallization to yield 2.4 g of Exemplified Compound 86 in the form of yellow powders. Yield: 66%.

$^{1}$H-NMR (300 MHz, CDCl$_{3}$) δ: 1.97 (s, 6H), 2.15 (s, 12H), 7.06 (s, 12H), 7.18 (s, 4H), 7.31 (s, 2H), 7.54 (t, J=28.2 Hz, 2H).

Example 15

<Synthesis of Exemplified Compound 87>

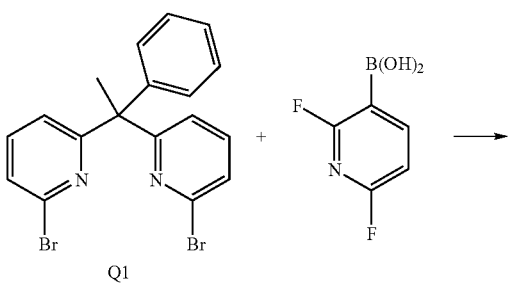

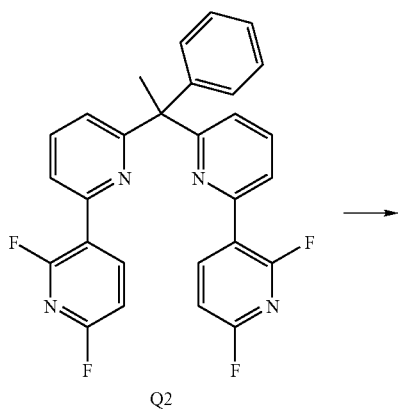

Q2

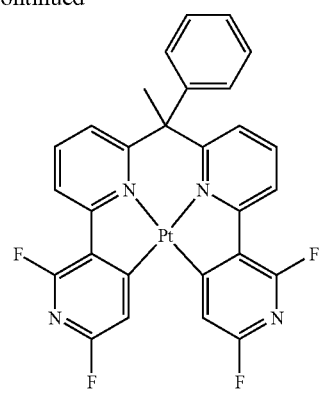

Exemplified Compound 87

Synthesis of Compound Q2

In a nitrogen atmosphere, a three-necked flask is charged with Compound Q1 (1.77 g, 4.23 mmol), 2,6-difluoropyridyl-3-boric acid (1.6 g, 10 mmol), palladium acetate (48 mg, 0.22 mmol), triphenylphosphine (221 mg, 0.846 mmol), sodium carbonate (4.48 g, 42.3 mmol), 1,2-dimethoxyethane (25 ml) and water (25 ml). The resulting mixture is heated under reflux for 6 hours while stirring. After cooling to room temperature, the reaction mixture is extracted with ethyl acetate. The organic layer thus obtained is dried over sodium sulfate and filtered, followed by concentration. The residue obtained is purified by silica gel column chromatography to yield 2.1 g of Compound Q2 in the form of a beige solid.

Synthesis of Exemplified Compound 87

In a nitrogen atmosphere, a 100-mL egg-plant type flask is charged with Compound Q2 (2.1 g, 4.31 mmol), platinum chloride (1.148 g, 4.31 mmol) and benzonitrile (30 mL), and the resulting mixture is stirred at 180° C. for 2 hours. After cooling to room temperature, the reaction mixture is admixed with 50 mL of methanol to precipitate a solid. The solid thus precipitated is filtered off, and dried under reduced pressure, thereby yielding 1.52 g (yield: 52%) of Exemplified Compound 87 in the form of yellow crystals.

$^{1}$H-NMR (CD$_{2}$Cl$_{2}$) 300 MHz δ: 2.20 (s, 3H), 6.60-6.66 (m, 2H), 7.22-7.33 (m, 3H), 7.39 (t, J=1.8 Hz, J(Pt—H)=55.8 Hz, 2H), 7.58-7.61 (m, 2H), 8.05 (t, J=8.1 Hz, 2H), 8.20 (d, J=8.1 Hz, 2H).

Example 16

<Synthesis of Exemplified Compound 96>

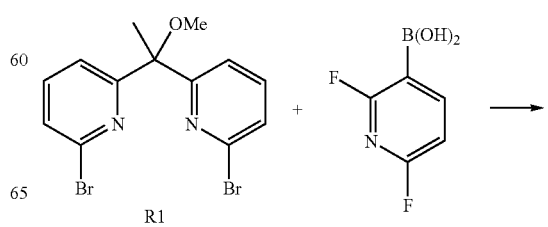

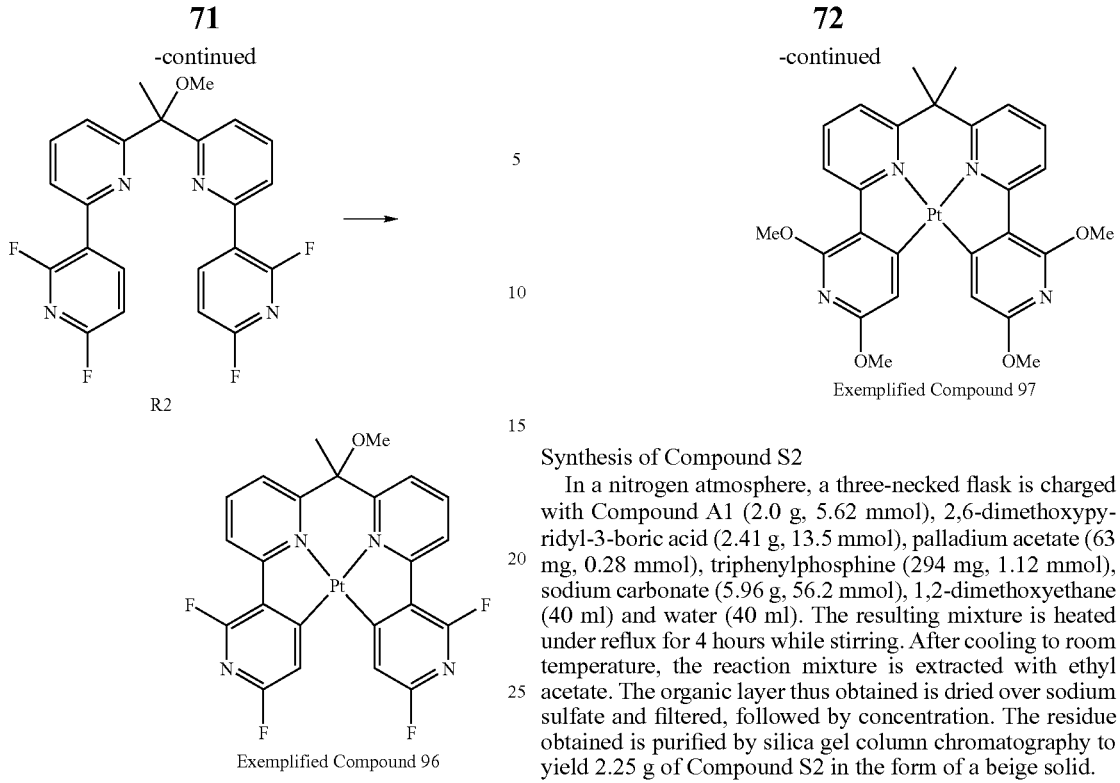

Exemplified Compound 97

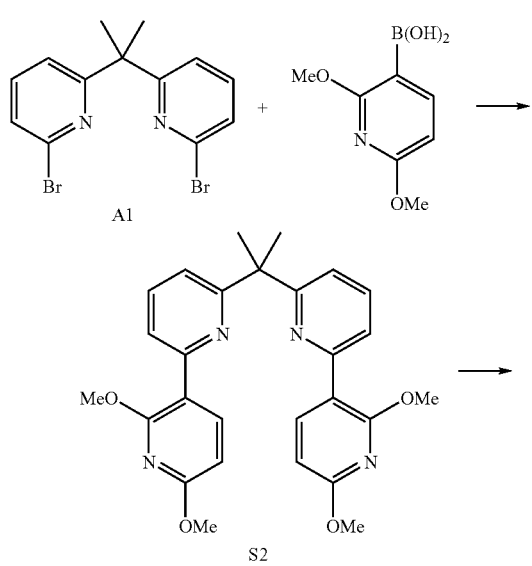

Exemplified Compound 96

Synthesis of Exemplified Compound 96 is performed by the same method as used in the synthesis of Exemplified Compound 43, except that Compound R1 is used as a raw material in place of Compound O1, thereby yielding Exemplified Compound 96 in the form of yellow crystals.

$^1$H-NMR (CD$_2$Cl$_2$) 300 MHz δ: 2.15 (s, 3H), 3.61 (s, 3H), 7.51 (s, J(Pt—H)=57 Hz, 2H), 7.70 (dd, J=2.4, 6.3 Hz, 2H), 7.94 (dt, J=2.4, 6.3 Hz, 2H).

Example 17

<Synthesis of Exemplified Compound 97>

Synthesis of Compound S2

In a nitrogen atmosphere, a three-necked flask is charged with Compound A1 (2.0 g, 5.62 mmol), 2,6-dimethoxypyridyl-3-boric acid (2.41 g, 13.5 mmol), palladium acetate (63 mg, 0.28 mmol), triphenylphosphine (294 mg, 1.12 mmol), sodium carbonate (5.96 g, 56.2 mmol), 1,2-dimethoxyethane (40 ml) and water (40 ml). The resulting mixture is heated under reflux for 4 hours while stirring. After cooling to room temperature, the reaction mixture is extracted with ethyl acetate. The organic layer thus obtained is dried over sodium sulfate and filtered, followed by concentration. The residue obtained is purified by silica gel column chromatography to yield 2.25 g of Compound S2 in the form of a beige solid.

Synthesis of Exemplified Compound 97

In a nitrogen atmosphere, a 100-mL egg-plant type flask is charged with Compound S2 (2.05 g, 4.34 mmol), K$_2$PtCl$_4$ (1.8 g, 4.34 mmol) and acetic acid (50 mL), and the resulting mixture is stirred at 100° C. for 8 hours. After cooling to room temperature, the reaction mixture is admixed with water, and extracted with chloroform. The organic layer obtained is dried over sodium sulfate, filtered, and then concentrated. The residue thus obtained is purified by silica gel column chromatography, thereby yielding 0.38 g of Exemplified Compound 97 in the form of yellow crystals.

$^1$H-NMR (CDCl$_3$) 300 MHz δ: 2.04 (s, 3H), 4.00 (s, 6H), 4.08 (s, 6H), 7.23 (s, 2H), 7.31 (dd, J=0.8, 8.1 Hz, 2H), 7.75 (t, J=8.1 Hz, 2H), 8.55 (dd, J=0.6, 8.1 Hz, 2H).

Comparative Example 1

The ligand C2 of the Compound (55) disclosed in International Patent Publication No. 2004-108857 and the ligand D2 (which each have no substituents at the α-positions of each pyridine ring which forms a platinum-carbon bond) are synthesized, and each of them is subjected to complexation reaction according to each of the same methods as in Examples 1 and 2. In every case, however, by-products are formed in large quantities, and the yield of the intended complex is 1% or below.

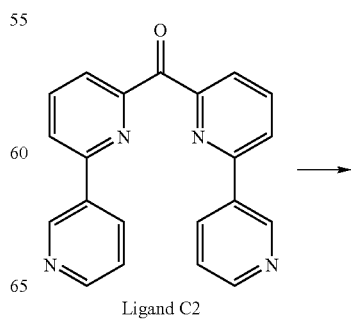

Ligand C2

-continued

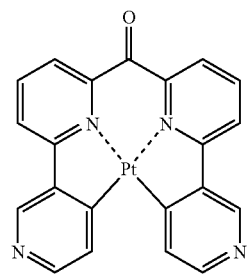

Compound 55 disclosed in
International Patent Publication No. 2004-108857

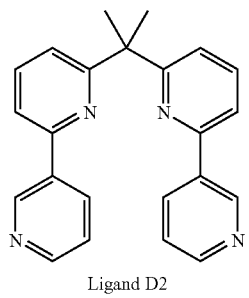

Ligand D2

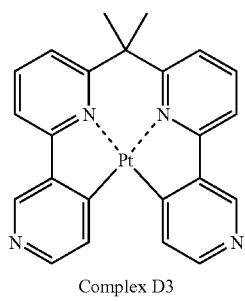

Complex D3

Example 18

A cleaned ITO substrate is placed in a vapor deposition apparatus, and copper phthalocyanine is deposited on the substrate at a thickness of 10 nm. Thereon, NPD ((N,N'-di-α-naphthyl-N,N'-diphenyl)benzidine) is deposited at a thickness of 40 nm. Thereon, mCP (a host material) and Exemplified Compound 3 in the invention are deposited in a ratio (mass ratio) of 85:15 at a thickness of 67 nm, and thereon BAlq is deposited at a thickness of 40 nm. Thereon, lithium fluoride is deposited at a thickness of 3 nm, and subsequently thereto aluminum is deposited at a thickness of 60 nm. In this way, an EL device is made. When light is made to emit from the EL device by applying thereto a direct-current constant voltage by means of Source Measure Unit 2400 manufactured by Toyo Corporation, the light emitted is blue light originating in Exemplified Compound 3. The half-value period of the luminance (the time required for the luminance to drop to 50% of the initial luminance) of this device is 1.05 times as long as that of the device of Comparative Example 2 when the device is driven at 360 cd/m$^2$ (emission area: 4 mm$^2$). By contrast, when the device is driven under a higher luminance condition of 1,000 cd/m$^2$ (emission area: 4 mm$^2$), the half-value period of the luminance of this device is 1.8 times as long as that of the device of Comparative Example 2.

Example 19 to Example 27

EL devices are made in the same manner as in Example 18, except that the materials shown in Table 1 are used as a host material and a light emitting material in each of their respective light emitting layers, and half-value periods of luminance of each device under conditions that the device is driven at 360 cd/m$^2$ (emission area: 4 mm$^2$) and 1,000 cd/m$^2$ (emission area: 4 mm$^2$) respectively are measured. Results obtained are shown in Table 1.

TABLE 1

| EL device | Host material used in light emitting layer | Light emitting material in light emitting layer | Half-value period of luminance (under drive at 360 cd/m$^2$) expressed as relative value, with Comparative Example 2 being taken as 1 | Half-value period of luminance (under drive at 1,000 cd/m$^2$) expressed as relative value, with Comparative Example 2 being taken as 1 |
|---|---|---|---|---|
| Comparative Example 1 | mCP | Compound 2 | 1 | 1 |
| Example 18 | mCP | Exemplified Compound 3 | 1.05 | 1.8 |
| Example 19 | mCP | Exemplified Compound 1 | 1.05 | 1.3 |
| Example 20 | mCP | Exemplified Compound 27 | 1.1 | 1.7 |
| Example 21 | mCP | Exemplified Compound 31 | 1.2 | 2.0 |
| Example 22 | mCP | Exemplified Compound 43 | 1.05 | 1.5 |
| Example 23 | mCP | Exemplified Compound 47 | 1.1 | 1.3 |
| Example 24 | mCP | Exemplified Compound 54 | 1.05 | 1.3 |
| Example 25 | mCP | Exemplified Compound 87 | 1.15 | 1.9 |
| Example 26 | Host 1 | Exemplified Compound 3 | 1.3 | 2.2 |
| Example 27 | Host 1 | Exemplified Compound 87 | 1.4 | 2.3 |

Comparative Example 2

A cleaned ITO substrate is placed in a vapor deposition apparatus, and copper phthalocyanine is deposited on the substrate at a thickness of 10 nm. Thereon, NPD ((N,N'-di-α-naphthyl-N,N'-diphenyl)benzidine) is deposited at a thickness of 40 nm. Thereon, mCP (a host material) and Compound 2 disclosed in JP-A2007-19462 are deposited in a ratio (mass ratio) of 85-15 at a thickness of 67 nm, and thereon BAlq is deposited at a thickness of 40 nm. Thereon, lithium fluoride is deposited at a thickness of 3 nm, and subsequently thereto aluminum is deposited at a thickness of 60 nm. In this way, an EL device is made. When light is made to emit from the EL device by applying thereto a direct-current constant voltage by means of Source Measure Unit 2400 manufactured by Toyo Corporation, the light emitted is blue light originating in Compound 2. The half-value period of the luminance of the device is 100 hours when the device is driven at 360 cd/m² (emission area: 4 mm²), while it is 35 hours when the device is driven under a higher luminance condition of 1,000 cd/m² (emission area: 4 mm²).

The following are chemical structures of the copper phthalocyanine, NPD, Compound 2 described in JP-A-2007-19462, mCP, Host 1 and BAlq.

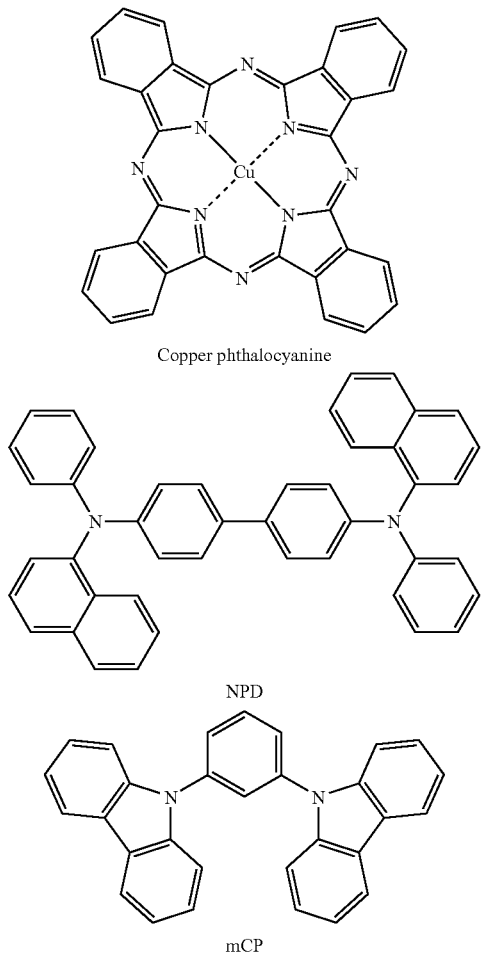

Copper phthalocyanine

NPD mCP

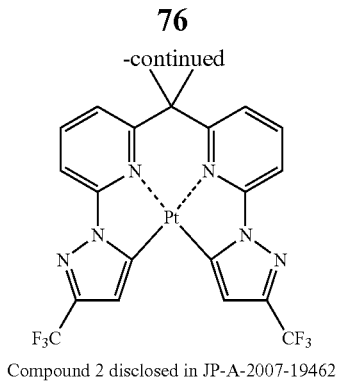

Compound 2 disclosed in JP-A-2007-19462

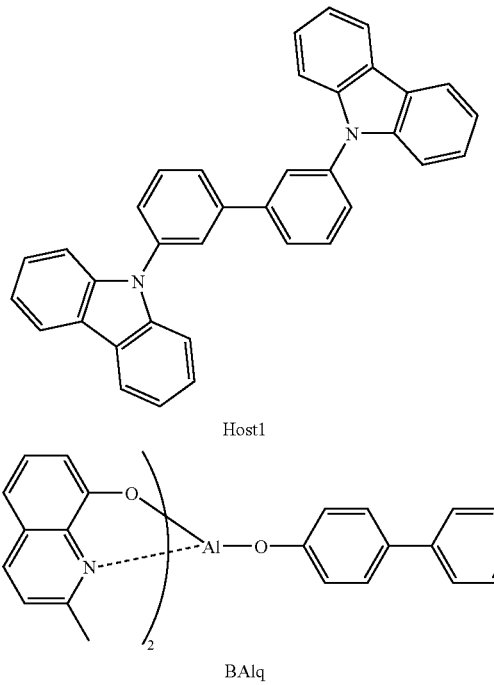

Host1

BAlq

An organic electroluminescence device obtained using another platinum complex of the invention also shows excellent durability even when it is used as a high luminance device.

The entire disclosure of each and every foreign patent application from which the benefit of foreign priority has been claimed in the present application is incorporated herein by reference, as if fully set forth.

What is claimed is:

1. A platinum complex represented by the following formula (1):

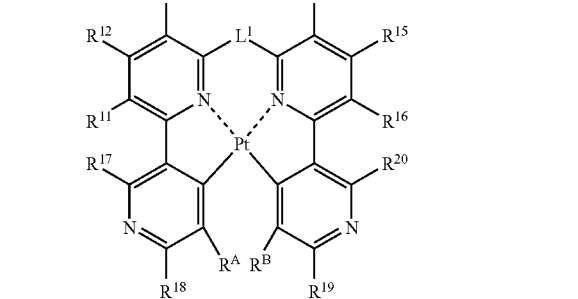

Formula (1)

wherein each of $R^{11}$, $R^{12}$, $R^{13}$, $R^{14}$, $R^{15}$, $R^{16}$, $R^A$ and $R^B$ independently represents a hydrogen atom or a substituent, each of $R^{17}$, $R^{18}$, $R^{19}$, and $R^{20}$ independently represents a hydrogen atom or a substituent, with the proviso that at least one of $R^{17}$ and $R^{18}$ represents an electron withdrawing substituent and at least one of $R^{19}$ and $R^{20}$ represents an electron withdrawing substituent, and $L^1$ represents a single bond or a divalent linking group.

2. A platinum complex according to claim 1, wherein the formula (1) is represented by the following formula (2):

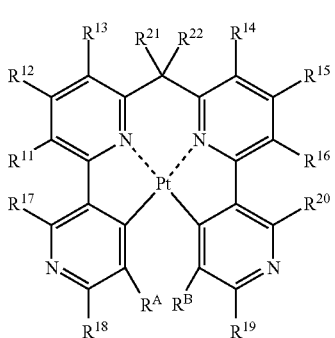

Formula (2)

wherein $R^{11}$, $R^{12}$, $R^{13}$, $R^{14}$, $R^{15}$, $R^{16}$, $R^{17}$, $R^{18}$, $R^{19}$, $R^{20}$, $R^A$ and $R^B$ have the same meanings as defined in the formula (1), and each of $R^{21}$ and $R^{22}$ independently represents a hydrogen atom or a substituent.

3. An organic electroluminescence device comprising:
a pair of electrodes; and
an organic layer between the pair of electrodes, which contains the platinum complex as claimed in claim 1.

4. An organic electroluminescence device comprising:
a pair of electrodes; and
an organic layer between the pair of electrodes, which comprises a light emitting layer containing the platinum complex as claimed in claim 1.

5. A process for preparing a platinum complex represented by the following formula (1), the process comprising:
reacting a compound represented by the following formula (B-2) and a compound represented by the following formula (B-2') with a compound represented by the following formula (A-0) to obtain a compound represented by the following formula (C-0); and
reacting the compound represented by the formula (C-0) with a platinum salt:

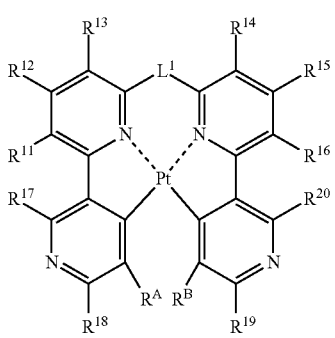

Formula (1)

wherein each of $R^{11}$, $R^{12}$, $R^{13}$, $R^{14}$, $R^{15}$, $R^{16}$, $R^A$ and $R^B$ independently represents a hydrogen atom or a substituent, each of $R^{17}$, $R^{18}$, $R^{19}$, and $R^{20}$ independently represents a hydrogen atom or a substituent, with the proviso that at least one of $R^{17}$ and $R^{18}$ represents an electron withdrawing substituent and at least one of $R^{19}$ and $R^{20}$ represents an electron withdrawing substituent, and $L^1$ represents a single bond or a divalent linking group,

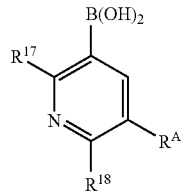

Formula (B-2)

wherein each of $R^{17}$ and $R^{18}$ independently represents a hydrogen atom or a substituent, with the proviso that at least one of $R^{17}$ and $R^{18}$ represents an electron withdrawing substituent, and $R^A$ represents a hydrogen atom or a substituent,

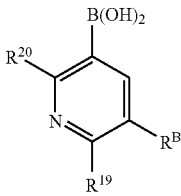

Formula (B-2')

wherein each $R^{19}$ and $R^{20}$ independently represents a hydrogen atom or a substituent, with the proviso that at least one of $R^{19}$ and $R^{20}$ represents an electron withdrawing substituent, and $R^B$ represents a hydrogen atom or a substituent,

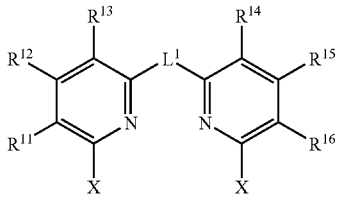

Formula (A-0)

wherein each of $R^{11}$, $R^{12}$, $R^{13}$, $R^{14}$, $R^{15}$, and $R^{16}$ independently represents a hydrogen atom or a substituent, $L^1$ represents a single bond or a divalent linking group, and X represents a halogen atom,

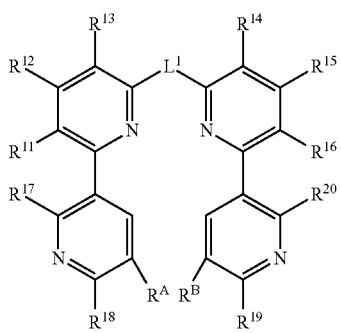

Formula (C-0)

wherein each of $R^{11}$, $R^{12}$, $R^{13}$, $R^{14}$, $R^{15}$, $R^{16}$, $R^A$ and $R^B$ independently represents a hydrogen atom or a substituent, each of $R^{17}$, $R^{18}$, $R^{19}$, and $R^{20}$ independently represents a hydrogen atom or a substituent, with the proviso that at least one of $R^{17}$ and $R^{18}$ represents an electron withdrawing substituent and at least one of $R^{19}$ and $R^{20}$ represents an electron withdrawing substituent, and $L^1$ represents a single bond or a divalent linking group.

6. A platinum complex obtained by the process as claimed in claim 5.

* * * * *